United States Patent
Lintereur et al.

(10) Patent No.: US 11,998,721 B2
(45) Date of Patent: *Jun. 4, 2024

(54) CONTINUOUS ANALYTE SENSOR QUALITY MEASURES AND RELATED THERAPY ACTIONS FOR AN AUTOMATED THERAPY DELIVERY SYSTEM

(71) Applicant: MEDTRONIC MINIMED, INC., Northridge, CA (US)

(72) Inventors: Louis J. Lintereur, Boise, ID (US); Alexander S. Campbell, Encino, CA (US); Dmytro Y. Sokolovskyy, Moorpark, CA (US); Neha J. Parikh, West Hills, CA (US); Maria Diana Miller, Santa Rosa Valley, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,877

(22) Filed: May 15, 2023

(65) Prior Publication Data
US 2023/0277768 A1 Sep. 7, 2023

Related U.S. Application Data

(63) Continuation of application No. 16/856,838, filed on Apr. 23, 2020, now Pat. No. 11,690,955.

(51) Int. Cl.
*A61M 5/172* (2006.01)
*G16H 10/40* (2018.01)
(Continued)

(52) U.S. Cl.
CPC .......... *A61M 5/1723* (2013.01); *G16H 10/40* (2018.01); *G16H 20/17* (2018.01); *G16H 40/67* (2018.01);
(Continued)

(58) Field of Classification Search
CPC ........ G16H 20/17; G16H 40/67; G16H 10/40; A61M 5/1723; A61M 2205/18;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| CN | 115426946 A | 12/2022 |
| EP | 4138656 A1 | 3/2023 |
| WO | 2021216155 A1 | 10/2021 |

OTHER PUBLICATIONS

U.S. Advisory Action dated Jan. 20, 2023 in U.S. Appl. No. 16/856,838.

(Continued)

*Primary Examiner* — Tammara R Peyton
(74) *Attorney, Agent, or Firm* — Weaver Austin Villeneuve & Sampson LLP

(57) ABSTRACT

Techniques disclosed herein relate to continuous analyte sensor quality measures. In some embodiments, the techniques may involve obtaining a current sensor-generated value that is indicative of a physiological characteristic of a user of a medical device, the current sensor-generated value produced in response to operation of a continuous analyte sensor device. The techniques may further involve obtaining a sensor quality metric that indicates accuracy of the current sensor-generated value. The techniques may further involve causing, in response to obtaining the sensor quality metric, configuration of a quality-specific operating mode of the medical device, the quality-specific operating mode comprising separate regulation of basal and bolus deliveries of a fluid medication based on the obtained sensor quality metric. The techniques may further involve causing regulation of (Continued)

fluid medication delivery from the medical device, in accordance with the current sensor-generated value and the quality-specific operating mode of the medical device.

20 Claims, 18 Drawing Sheets

(51) Int. Cl.
*G16H 20/17* (2018.01)
*G16H 40/67* (2018.01)

(52) U.S. Cl.
CPC . *A61M 2205/18* (2013.01); *A61M 2205/3584* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/702* (2013.01); *A61M 2230/201* (2013.01)

(58) Field of Classification Search
CPC ........ A61M 2205/502; A61M 2205/52; A61M 2205/702; A61M 2230/201
See application file for complete search history.

(56) References Cited

U.S. PATENT DOCUMENTS

| | | | |
|---|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van et al. |
| 8,353,829 B2 | 1/2013 | Say et al. |
| 8,474,332 B2 | 7/2013 | Bente, IV et al. |
| 8,674,288 B2 | 3/2014 | Hanson et al. |
| 9,457,146 B2 | 10/2016 | Dobbles et al. |
| 9,533,096 B2 | 1/2017 | Lebel et al. |
| 9,757,510 B2 | 9/2017 | Finan |
| 11,583,631 B2 | 2/2023 | Campbell et al. |
| 11,690,955 B2 * | 7/2023 | Lintereur ............ A61M 5/1723 604/504 |
| 2007/0123819 A1 | 5/2007 | Mernoe et al. |
| 2010/0160861 A1 | 6/2010 | Causey, III et al. |
| 2014/0066889 A1 | 3/2014 | Grosman et al. |
| 2014/0182350 A1 | 7/2014 | Bhavaraju et al. |
| 2017/0348483 A1 | 12/2017 | Duke et al. |
| 2018/0185578 A1 | 7/2018 | Monirabbasi et al. |
| 2019/0133506 A1 | 5/2019 | Ringemann |
| 2021/0060249 A1 | 3/2021 | Golenberg et al. |
| 2021/0330882 A1 | 10/2021 | Campbell et al. |
| 2021/0330883 A1 | 10/2021 | Lintereur et al. |

OTHER PUBLICATIONS

U.S. Final office Action dated Oct. 27, 2022 in U.S. Appl. No. 16/856,838.

U.S. Non-Final Office Action dated Jul. 11, 2022, in U.S. Appl. No. 16/856,838.

(56) References Cited

OTHER PUBLICATIONS

U.S. Notice of Allowance dated Aug. 23, 2022 in U.S. Appl. No. 16/856,830.
U.S. Notice of Allowance dated Dec. 16, 2022 in U.S. Appl. No. 16/856,830.
U.S. Notice of Allowance dated Feb. 21, 2023 in U.S. Appl. No. 16/856,838.
U.S. Notice of Allowance dated Jun. 5, 2023, in U.S. Appl. No. 16/856,838.

* cited by examiner

| | |
|---|---|
| BOLUS | 12:01 AM |
| NO GLUCOSE ← 1702 | 0.0 U |
| CARBS 0g | 0.0 U |
| BOLUS | 0.0 U |
| DETAILS | |
| DELIVER BOLUS | |

## CONTINUOUS ANALYTE SENSOR QUALITY MEASURES AND RELATED THERAPY ACTIONS FOR AN AUTOMATED THERAPY DELIVERY SYSTEM

CROSS-REFERENCE TO RELATED APPLICATIONS

This application is a continuation of U.S. patent application Ser. No. 16/856,838, filed Apr. 23, 2020, the entire contents of which are herein incorporated by reference for all purposes.

TECHNICAL FIELD

Embodiments of the subject matter described herein relate generally to a system that delivers therapy (e.g., medicine) to a user. More specifically, the subject matter described herein relates to user interface and quality checking features of an insulin infusion system that obtains glucose readings from a continuous glucose sensor.

BACKGROUND

Medical therapy delivery systems, such as fluid infusion pump devices, are relatively well known in the medical arts, for use in delivering or dispensing an agent, such as insulin or another prescribed medication, to a patient. A typical infusion pump includes a pump drive system that usually includes a small motor and drive train components that convert rotational motor motion to a translational displacement of a plunger (or stopper) in a fluid reservoir, which delivers medication from the reservoir to the body of a patient via a fluid path created between the reservoir and the body of a patient. Use of infusion pump therapy has been increasing, especially for delivering insulin for diabetics.

Control schemes have been developed to allow insulin infusion pumps to monitor and regulate a patient's blood glucose level in a substantially continuous and autonomous manner. Managing a diabetic's blood glucose level is complicated by variations in a patient's daily activities (e.g., exercise, carbohydrate consumption, and the like) in addition to variations in the patient's individual insulin response and potentially other factors. Some control schemes may attempt to proactively account for daily activities to minimize glucose excursions. At the same time, patients may manually initiate delivery of insulin prior to or contemporaneously with consuming a meal (e.g., a meal bolus or correction bolus) to prevent spikes or swings in the patient's blood glucose level that could otherwise result from the impending consumption of carbohydrates and the response time of the control scheme.

BRIEF SUMMARY

Techniques disclosed herein relate to continuous analyte sensor quality measures. The techniques may be practiced with a processor-implemented method, a system comprising one or more processors and one or more processor-readable media, and/or one or more non-transitory processor-readable media.

In some embodiments, the techniques may involve obtaining a current sensor-generated value that is indicative of a physiological characteristic of a user of a medical device, the current sensor-generated value produced in response to operation of a continuous analyte sensor device. The techniques may further involve obtaining a sensor quality metric that indicates accuracy of the current sensor-generated value. The techniques may further involve causing, in response to obtaining the sensor quality metric, configuration of a quality-specific operating mode of the medical device, the quality-specific operating mode comprising separate regulation of basal and bolus deliveries of a fluid medication based on the obtained sensor quality metric. The techniques may further involve causing regulation of fluid medication delivery from the medical device, in accordance with the current sensor-generated value and the quality-specific operating mode of the medical device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 17 is a schematic representation of a therapy delivery control screen on an insulin infusion device, with neither a BG value nor an SG value displayed thereon;

DETAILED DESCRIPTION

Figure 1:
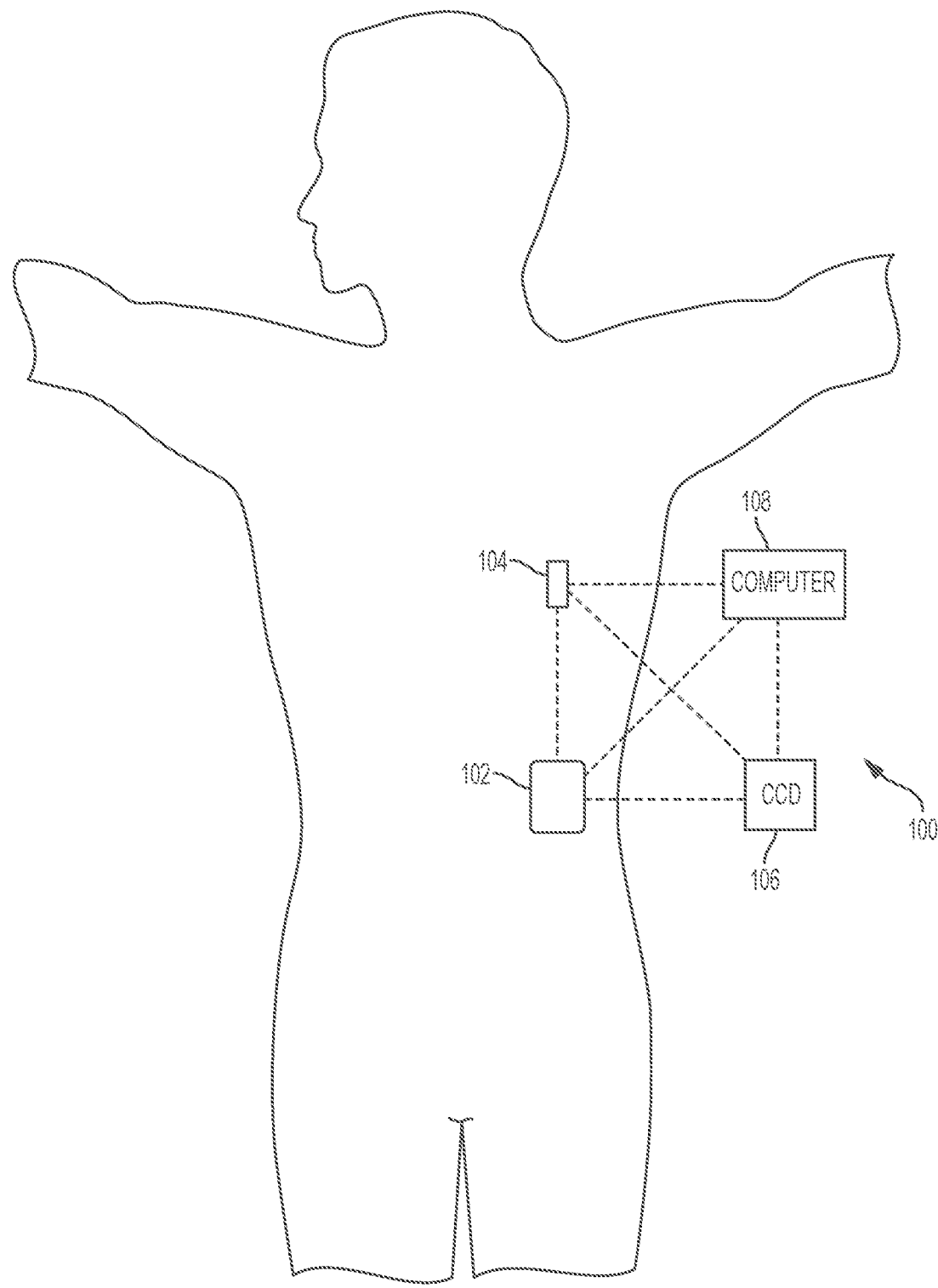
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate an insulin infusion device (or insulin pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

An insulin infusion pump can be operated in an automatic mode wherein basal insulin is delivered at a rate that is automatically adjusted for the user. While controlling the delivery of basal insulin in this manner, the pump can also control the delivery of correction boluses to account for rising glucose trends due to meals, stress, hormonal fluctuations, etc. Ideally, the amount of a correction bolus should be accurately calculated and administered to maintain the user's blood glucose within the desired range. In particular, an automatically generated and delivered correction bolus should safely manage the user's blood glucose level and keep it above a defined hypoglycemic threshold level.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In some embodiments, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
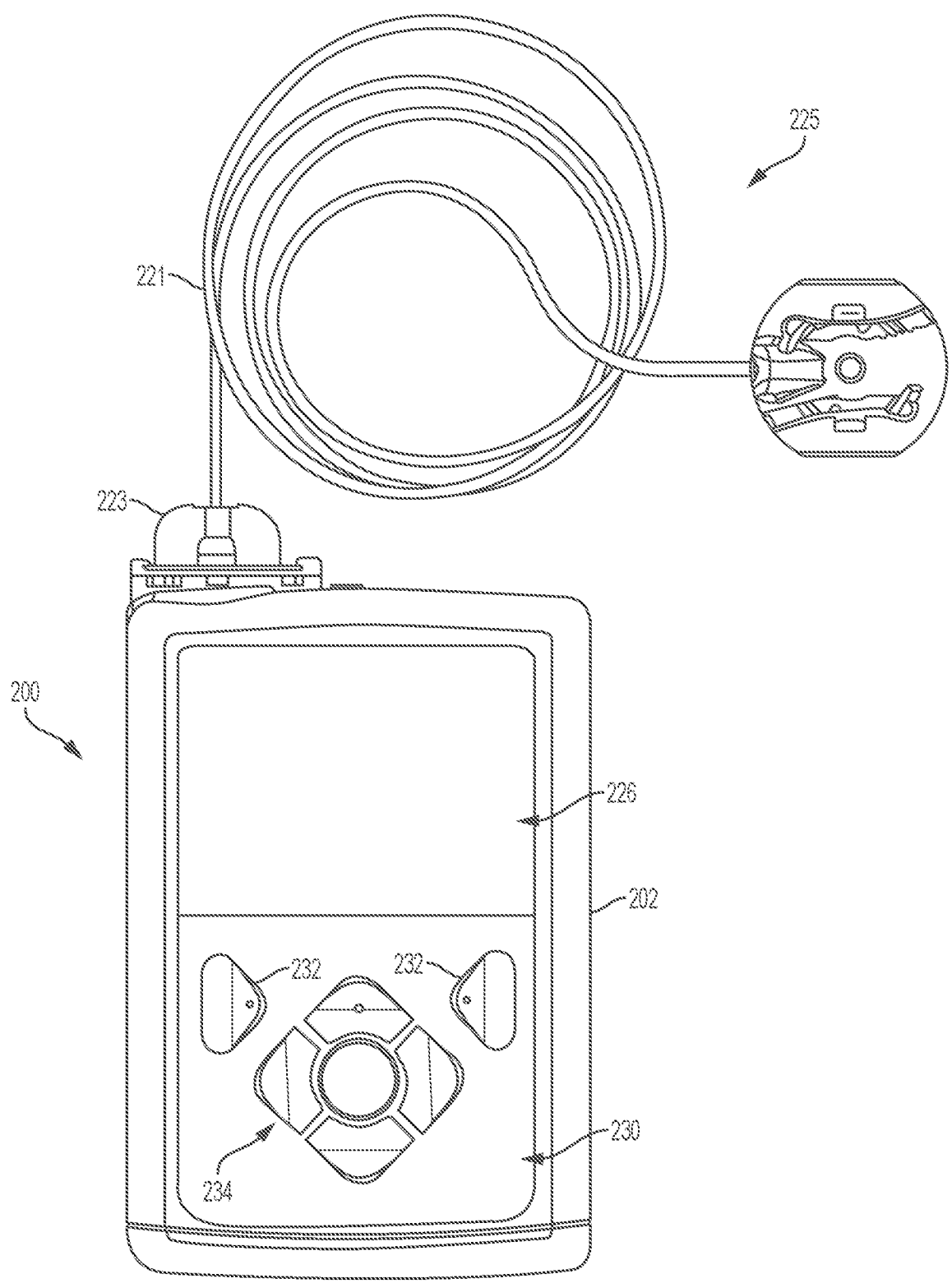
FIG. 2 depicts a plan view of an exemplary embodiment of a fluid infusion device suitable for use in the infusion system of FIG. 1.
Figure 3:
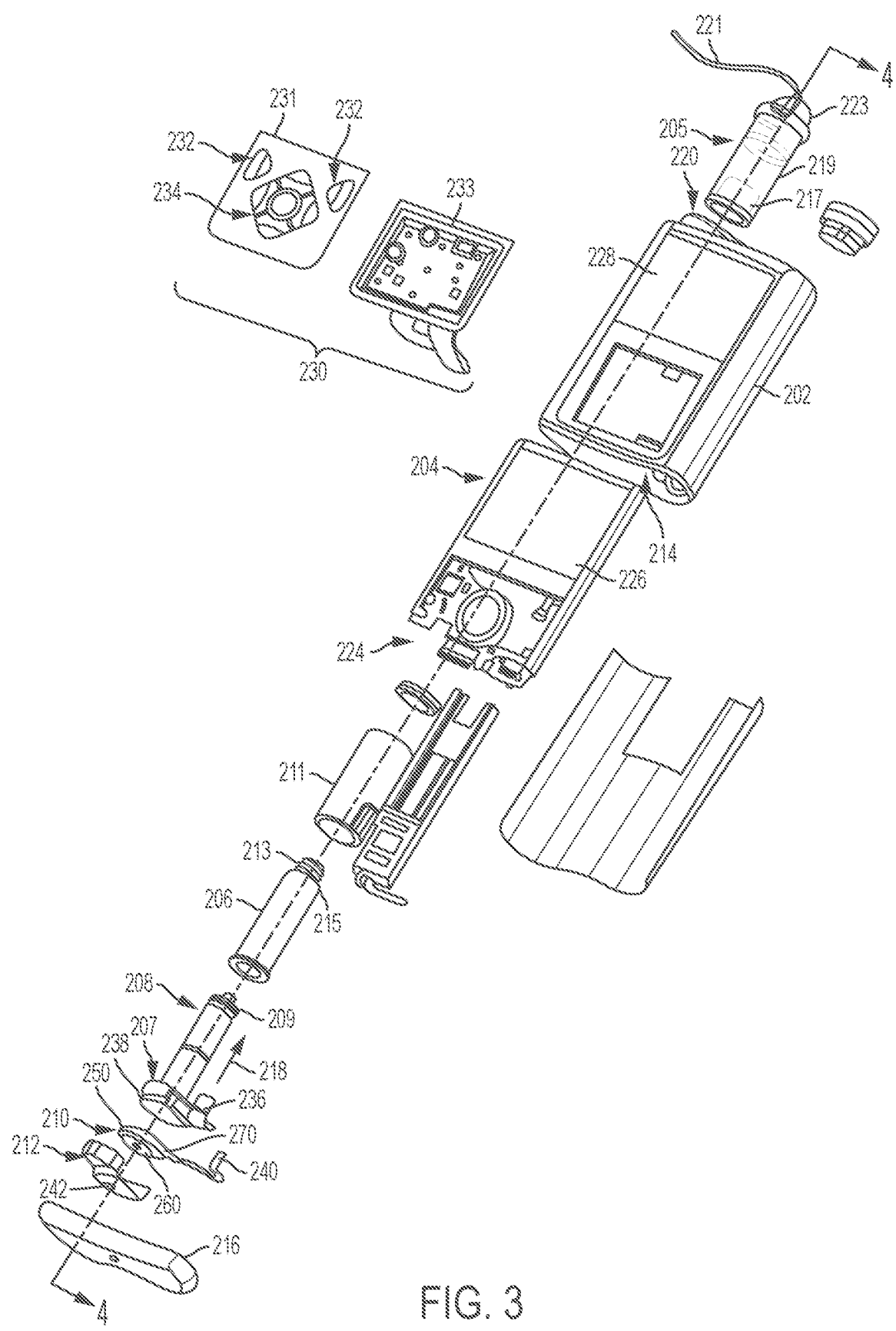
FIG. 3 is an exploded perspective view of the fluid infusion device of FIG. 2.
Figure 4:
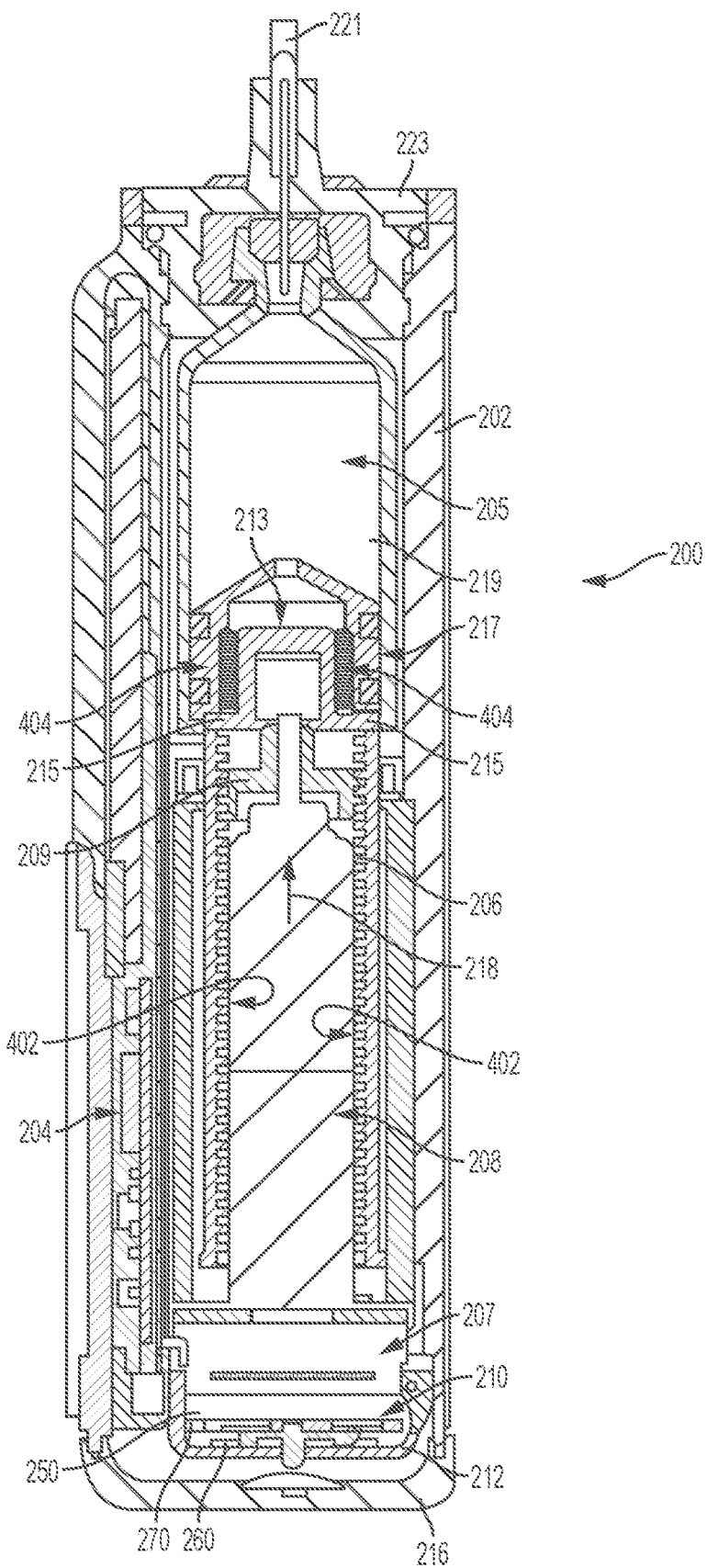
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in some embodiments, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display device 226, such as a liquid crystal display (LCD) or another suitable display device, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion device 200 is subjected to shock or vibration; when the infusion device 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion device 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion device 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion device 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display device 226, with the housing 202 including a transparent window portion 228 that is aligned with the display device 226 to allow the display device 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. The control electronics 224 is also suitably configured and designed to support various user interface, input/output, and display features of the fluid infusion device 200. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion device 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion device 200, for example, to administer a bolus of insulin, to change therapy settings, to change user preferences, to select display features, to set or disable alarms and reminders, and the like. In this regard, the control electronics 224 maintains and/or provides information to the display device 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., graphical user interface elements that use touch-sensing and/or proximity-sensing technologies). For example, in some embodiments, the display device 226 may be realized as a touch screen or touch-sensitive display, and in such embodiments, the features and/or functionality of the HMI elements 232, 234 may be integrated into the display device 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing capping member 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of the arrow that represents the axial direction 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
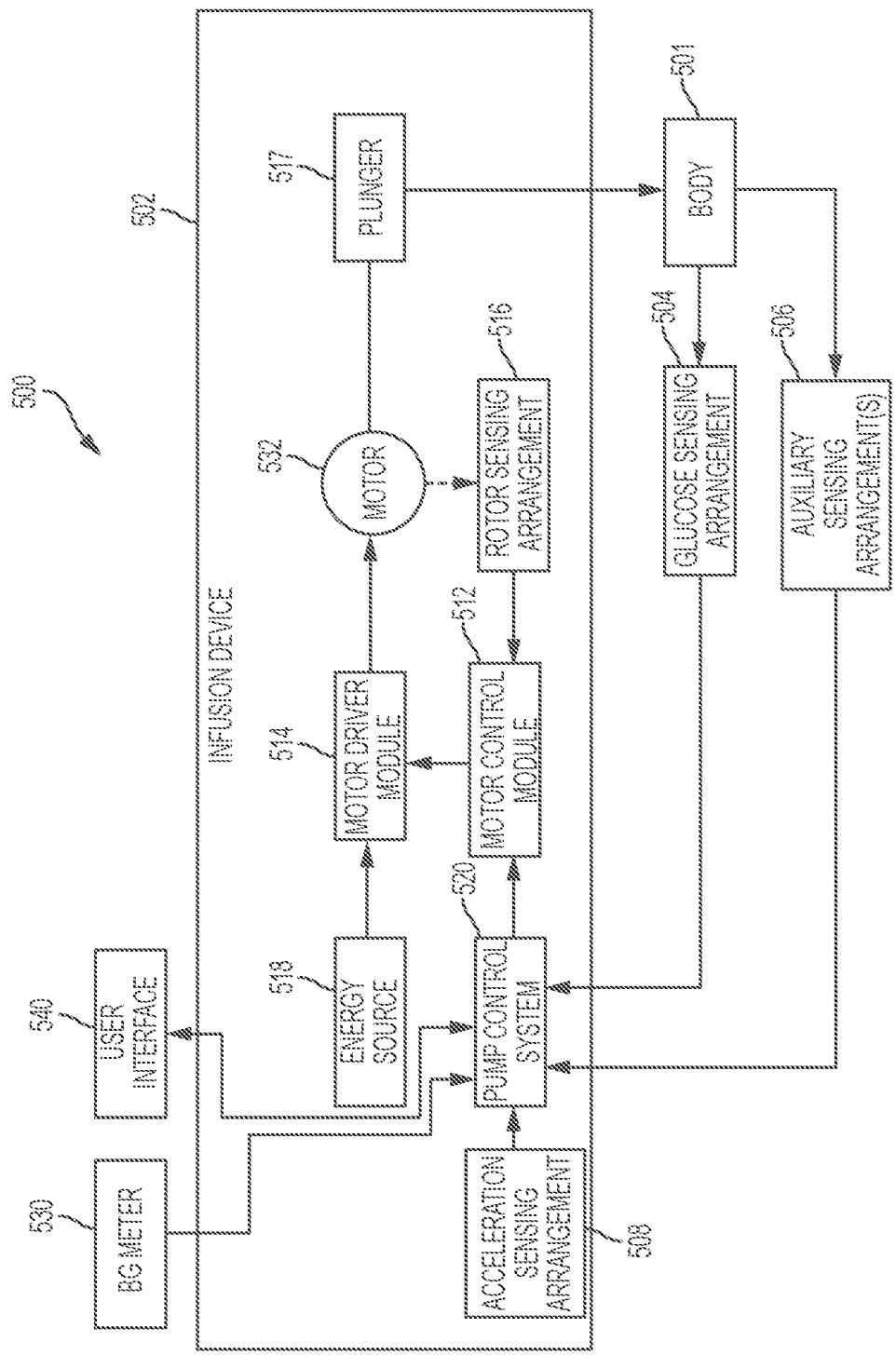
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., a blood glucose sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the patient's glucose level, which is being regulated in the body 501 of the patient by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the patient. The output electrical signals are filtered or otherwise processed to obtain a measurement value indicative of the patient's interstitial fluid glucose level. In exemplary embodiments, a blood glucose meter 530, such as a finger stick device, is utilized to directly sense, detect, measure or otherwise quantify the blood glucose in the body 501 of the patient. In this regard, the blood glucose meter 530 outputs or otherwise provides a measured blood glucose value that may be utilized as a reference measurement for calibrating the sensing arrangement 504 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the patient that is indicative of a condition in the body 501 of the patient. In this regard, in addition to the glucose sensing arrangement 504, one or more auxiliary sensing arrangements 506 may be worn, carried, or otherwise associated with the body 501 of the patient to measure characteristics or conditions of the patient (or the patient's activity) that may influence the patient's glucose levels or insulin sensitivity. For example, a heart rate sensing arrangement 506 could be worn on or otherwise associated with the patient's body 501 to sense, detect, measure or otherwise quantify the patient's heart rate, which, in turn, may be indicative of exercise (and the intensity thereof) that is likely to influence the patient's glucose levels or insulin response in the body 501. In yet another embodiment, another invasive, interstitial, or subcutaneous sensing arrangement 506 may be inserted into the body 501 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the patient, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the patient's body 501 to sense, detect, measure or otherwise quantify an acceleration of the patient's body 501, which, in turn, may be indicative of exercise or some other condition in the body 501 that is likely to influence the patient's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the patient, or the acceleration sensing arrangement 508 may be realized as a separate standalone component that is worn by the patient.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the patient. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the patient based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In some embodiments, the infusion device 502 may store or otherwise maintain the target value, upper and/or lower glucose limit(s), insulin delivery limit(s), and/or other glucose threshold value(s) in a data storage element accessible to the pump control system 520. As described in greater detail, in one or more exemplary embodiments, the pump control system 520 automatically adjusts or adapts one or more parameters or other control information used to generate commands for operating the motor 532 in a manner that accounts for a likely change in the patient's glucose level or insulin response resulting from a meal, exercise, or other activity.

Still referring to FIG. 5, the target glucose value and other threshold glucose values utilized by the pump control system 520 may be received from an external component (e.g., CCD 106 and/or computing device 108) or be input by a patient via a user interface element 540 associated with the infusion device 502. In some embodiments, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display device (e.g., a light-emitting diode or the like), a display device (e.g., a liquid crystal display or the like), a speaker or another audio output device, a haptic feedback device, or the like, for providing notifications or other information to the patient. It should be noted that although FIG. 5 depicts the user interface element(s) 540 as being separate from the infusion device 502, in some embodiments, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the patient to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a patient. In this regard, displacement of the plunger 517 results in the delivery of a fluid, such as insulin, that is capable of influencing the patient's physiological condition to the body 501 of the patient via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the patient.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in some embodiments, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
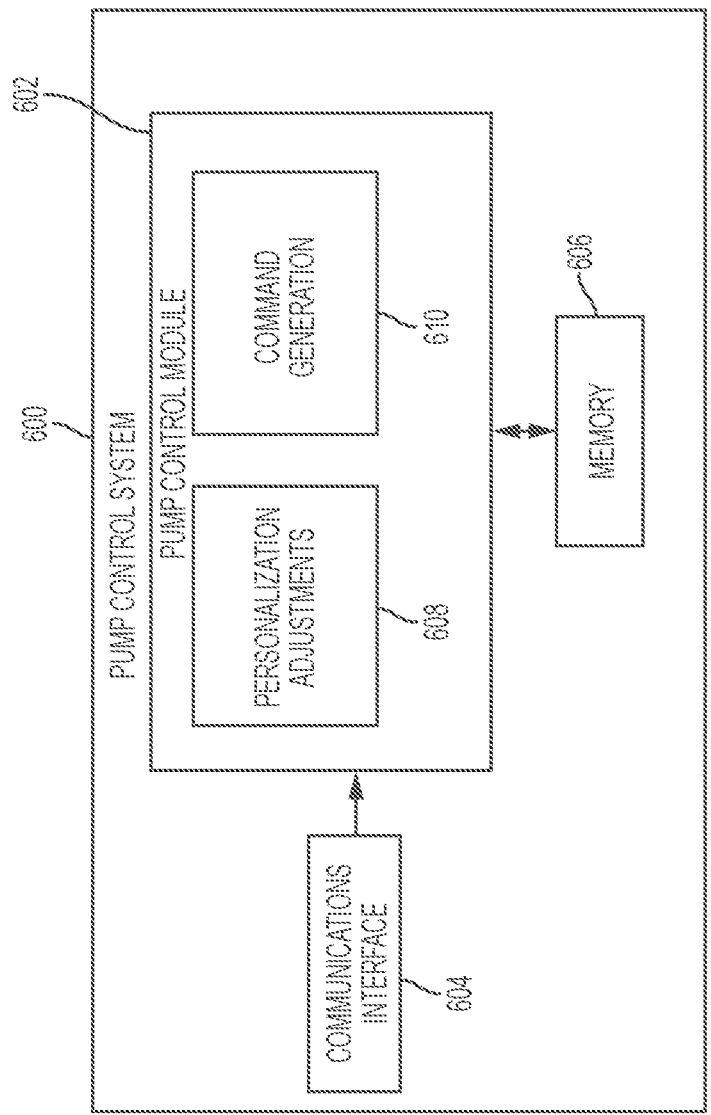
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the patient.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the patient. For example, in a closed-loop operating mode, the command generation application 610 may determine a dosage command for operating the motor 532 to deliver insulin to the body 501 of the patient based at least in part on the current glucose measurement value most recently received from the sensing arrangement 504 to regulate the patient's blood glucose level to a target reference glucose value. Additionally, the command generation application 610 may generate dosage commands for boluses that are manually-initiated or otherwise instructed by a patient via a user interface element.

In exemplary embodiments, the pump control module 602 also implements or otherwise executes a personalization application 608 that is cooperatively configured to interact with the command generation application 610 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 608 may adjust or otherwise modify values for one or more parameters utilized by the command generation application 610 when determining dosage commands, for example, by modifying a parameter value at a register or location in memory 606 referenced by the command generation application 610. In yet other embodiments, the personalization application 608 may predict meals or other events or activities that are likely to be engaged in by the patient and output or otherwise provide an indication of the predicted patient behavior for confirmation or modification by the patient, which, in turn, may then be utilized to adjust the manner in which dosage commands are generated to regulate glucose in a manner that accounts for the patient's behavior in a personalized manner.

Still referring to FIG. 6, depending on the embodiment, the pump control module 602 may be implemented or realized with at least one general purpose processor device, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
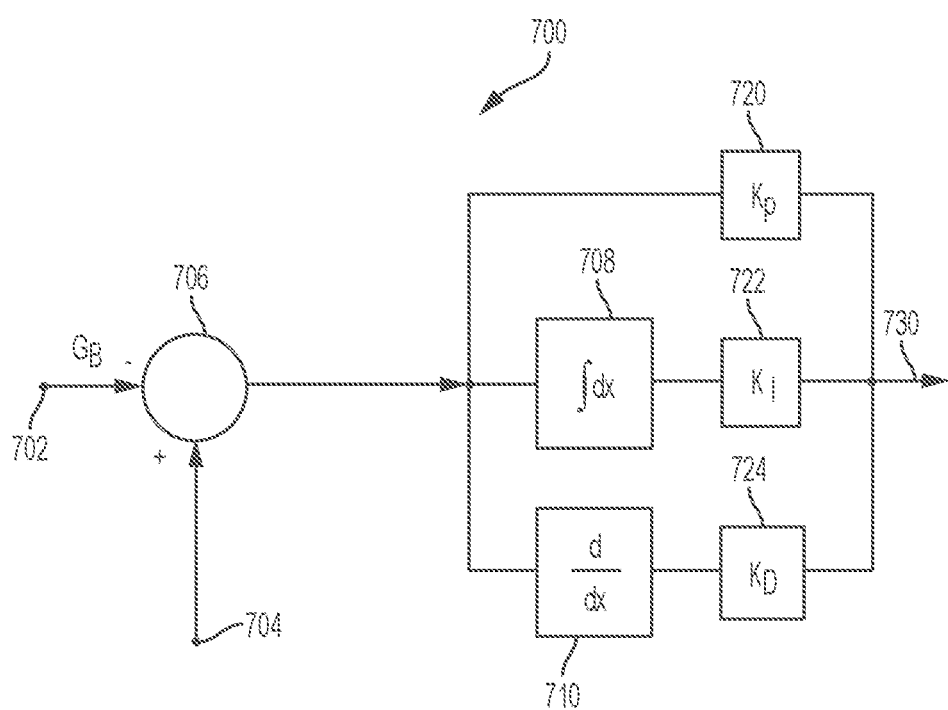
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a patient to a reference (or target) value. In this regard, the control system 700 can be utilized to regulate the delivery of insulin to the patient during an automatic basal insulin delivery operation. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 532 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 532 to deliver insulin to the body of the patient to influence the patient's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, KP, to obtain the proportional term. The integral term path includes an integration block 708 that integrates the difference and a gain block 722 that multiplies the integrated difference by an integral gain coefficient, KI, to obtain the integral term. The derivative term path includes a derivative block 710 that determines the derivative of the difference and a gain block 724 that multiplies the derivative of the difference by a derivative gain coefficient, KD, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

In one or more exemplary embodiments, one or more parameters of the closed-loop control system 700 are automatically adjusted or adapted in a personalized manner to account for potential changes in the patient's glucose level or insulin sensitivity resulting from meals, exercise, or other events or activities. For example, in one or more embodiments, the target glucose value may be decreased in advance of a predicted meal event to achieve an increase in the insulin infusion rate to effectively pre-bolus a meal, and thereby reduce the likelihood of postprandial hyperglycemia. Additionally or alternatively, the time constant or gain coefficient associated with one or more paths of the closed-loop control system 700 may be adjusted to tune the responsiveness to deviations between the measured glucose value and the target glucose value. For example, based on the particular type of meal being consumed or the particular time of day during which the meal is consumed, the time constant associated with the derivative block 710 or derivative term path may be adjusted to make the closed-loop control more or less aggressive in response to an increase in the patient's glucose level based on the patient's historical glycemic response to the particular type of meal.

Figure 8:
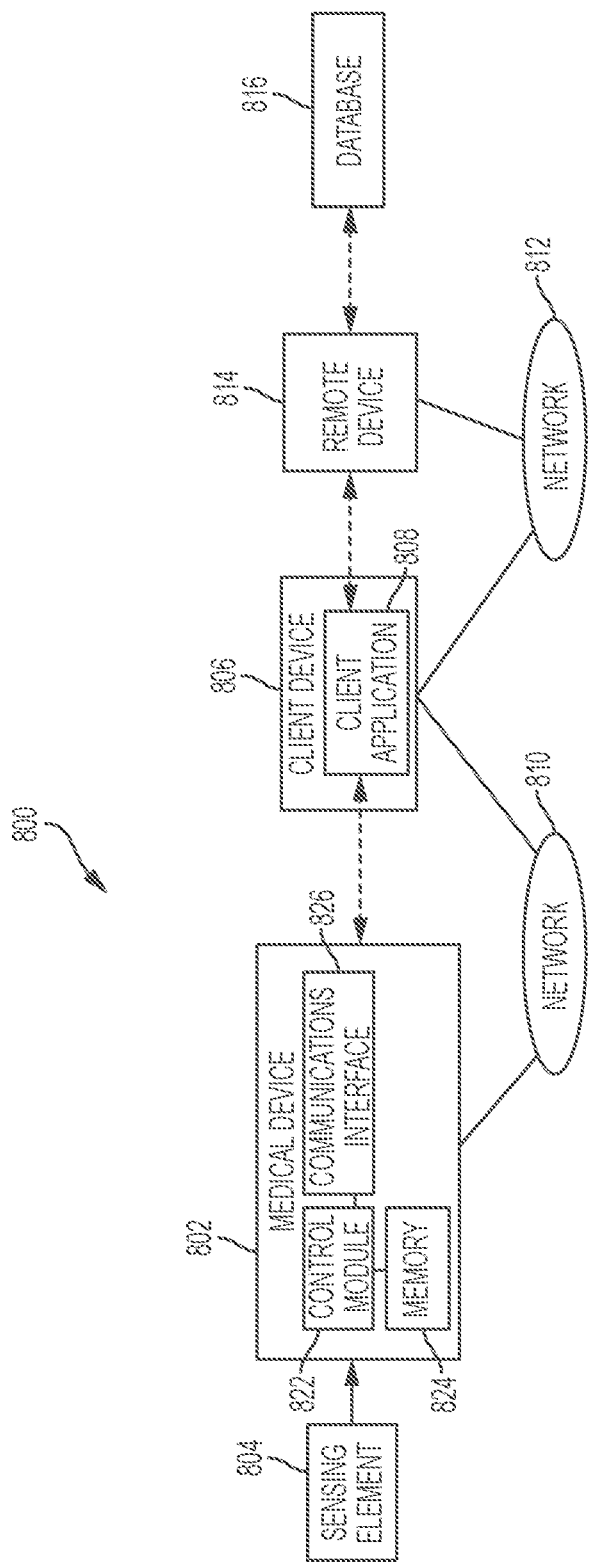
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processor devices, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In some embodiments, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a patient influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the remote device 814 or server via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504). It should be noted that although FIG. 8 depicts the medical device 802 and the sensing element 804 as separate components, in some embodiments, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor device, a microprocessor device, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time.

The historical patient data may be analyzed by one or more of the remote device 814, the client device 806, and/or the medical device 802 to alter or adjust operation of an infusion device 102, 200, 502 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

A medical device of the type described herein can generate various user interface display screens that support different functions and features. For example, an insulin infusion device can generate a home screen that serves as a patient status or monitoring screen, a settings/preferences screen, a bolus delivery control screen, and the like. These and other display screens can present the user with different information, status data, notifications, patient data (e.g., glucose data), and/or other information in any desired arrangement or format.

Non-adjunctive insulin administration requires a sensor glucose (SG) value to be presented for bolus dosage estimation. The SG value should only be presented to the user when it is accurate, reliable, or otherwise trusted. A user may instead choose to use a blood glucose (BG) value from a linked blood glucose meter device (e.g., a blood glucose meter device in wireless or wired communication with the medical device). Given that there are two sources of inputs for therapy, and only one source may be used, the insulin infusion device is suitably configured to clearly indicate which glucose source is being used. To this end, the exemplary embodiment described here is controlled in an appropriate manner to avoid using a current SG value for bolus estimation when it is determined that the quality or reliability of the SG value is not sufficiently high. The exemplary embodiment also safely disambiguates SG from BG, for purposes of bolus estimation and presentation to the user.

The operating methodology described in more detail below is governed by certain rules when handling BG and SG values. For example, when a BG value is provided to the system, that value is displayed on a bolus delivery control screen until the BG value is expired (e.g., after a designated period of time, such as 12 minutes). A unique and visually distinguishable icon is used to indicate that the displayed value is a BG value. If the user fails to make a bolus delivery selection within a predefined period of time (e.g., 12 minutes or any other period of time), the bolus delivery feature will timeout.

In accordance with another operating rule, when an SG value is trusted by the system and there is no recent BG entry, the bolus delivery control screen includes the current SG value with a corresponding icon in a manner that is visually distinguishable from a displayed BG value. The SG value displayed within the bolus delivery screen cannot be modified via the user interface of the insulin infusion device.

In accordance with another operating rule, if there is a sudden spike in SG readings (e.g., the SG increases at a rate that is higher than a predetermined threshold value) that cannot be attributed to carbohydrate ingestion or other physiological processes, the current SG value is assumed to be temporarily unsuitable for non-adjunctive therapy. In that instance, no alert is required, but the SG value is not presented on the bolus delivery control screen, and the SG value is not used to calculate a bolus estimate.

Accordingly, the insulin infusion device supports a user interface associated with fully non-adjunctive bolus estimation. The current SG value is intuitively displayed in the bolus delivery control screen when it is a stable/trusted value. Otherwise, the SG value is removed from the bolus delivery control screen without generating a user alert. If the user desires to administer a manual bolus, then user can provide a BG value to be used for bolus estimation. The display screens and user interface features are designed such that the SG value is clearly disambiguated from the BG value. This avoids user confusion and potential bolus estimation errors.

Figure 9:
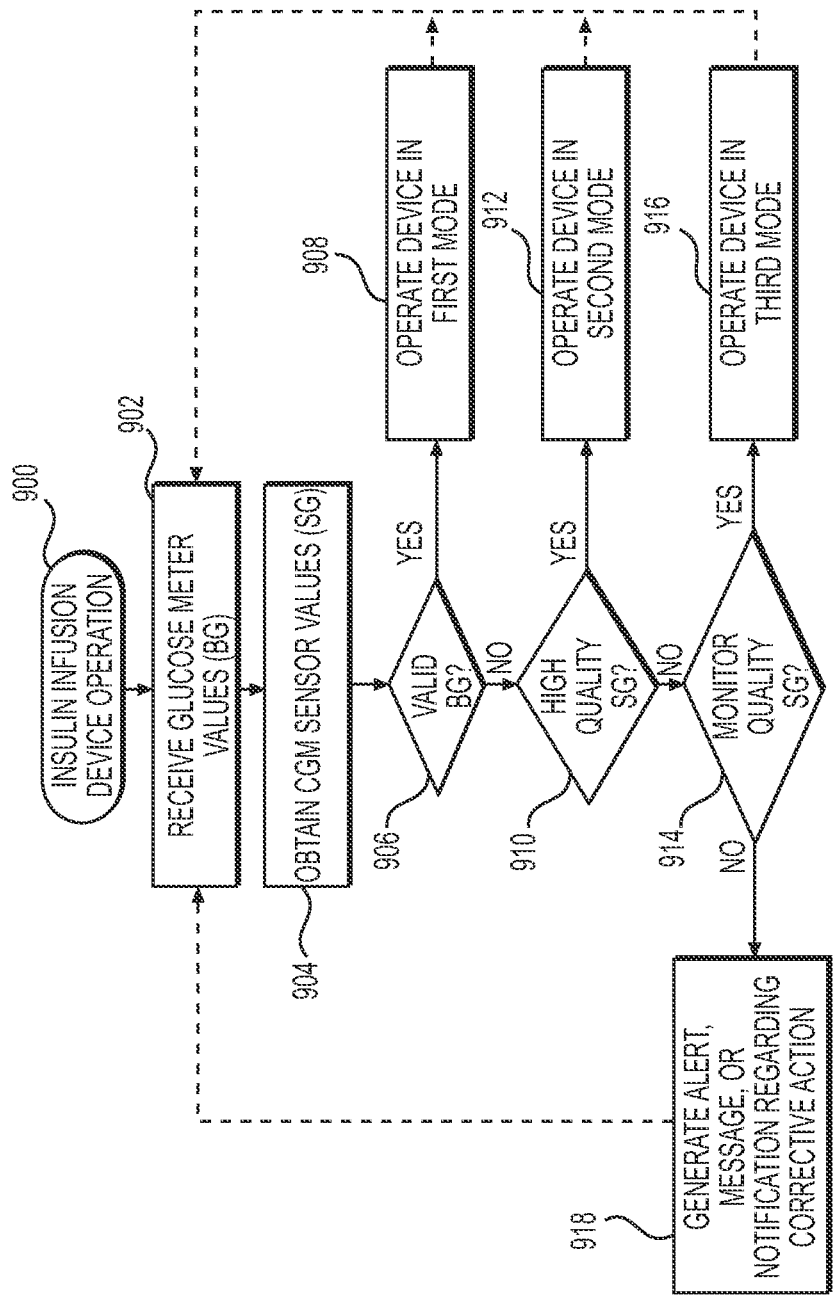
FIG. 9 is a flow chart that illustrates an exemplary embodiment of a process for operating a medical device, such as an insulin infusion device.

FIG. 9 is a flow chart that illustrates an exemplary embodiment of a process 900 for operating a medical device that regulates delivery of a fluid medication to a user. The process 900 may be performed by an insulin infusion device of the type described above or any other medical device. The process 900 receives meter-generated values that are indicative of a physiological characteristic of the user, wherein the generated values are produced in response to operation of an analyte meter device. For the exemplary implementation described here, the medical device is an insulin infusion device, the fluid medication is insulin, the physiological characteristic of interest is blood glucose, and the meter-generated values are BG values obtained from a blood glucose meter device (e.g., a BG fingerstick device) that generates BG measurements from a blood sample taken from the user. Thus, the exemplary embodiment of the process 900 receives BG values (e.g., once a day, every 12 hours, or as often as desired by the user), either directly from a linked BG meter or via manual data entry by a user or caregiver at the insulin infusion device (task 902). The insulin infusion device assumes that recently received BG measurements (whether they are user-entered or received directly from a BG meter device) are accurate and trustworthy.

The process 900 also obtains sensor-generated values that are indicative of the same physiological characteristic of the user, wherein the sensor-generated values are produced in response to operation of a continuous analyte sensor device. For the exemplary insulin infusion device implementation described here, the sensor-generated values are SG values obtained from a continuous glucose monitor or sensor (or calculated from sensor data obtained from a continuous glucose monitor or sensor) that is worn by the user. Thus, the exemplary embodiment of the process 900 obtains SG values periodically, e.g., every five minutes, every ten minutes, or any other desired period of time (task 904). In some embodiments, tasks 902 and 904 are performed independently of one another. For example, task 904 may be performed more often than task 902, or tasks 902 and 904 may be performed serially in any order or concurrently.

The process 900 determines how to use the BG value and/or the SG value for display purposes and for therapy dosage and delivery purposes. To this end, the exemplary embodiment of the process 900 checks for the presence of a valid BG value, e.g., a valid meter-generated value (query task 906). For this particular implementation, a current BG value is deemed to be "valid" until it expires after an expiration time period. The expiration time period may vary from one embodiment to another. For this particular example, BG values have a valid lifespan of only 12 minutes; stale BG values are not used. Thus, if the process 900 determines that a valid BG value is available (the "Yes" branch of query task 906), then the device is controlled in an appropriate manner to operate in a first mode, e.g., as described in further detail with respect to FIG. 10 below (task 908). In accordance with the embodiment described here, the device is operated in the first mode when a valid meter-generated BG value is available, regardless of the availability of a sensor-generated SG value, and regardless of the quality, accuracy, or trustworthiness of the current SG value (if one is available).

Figure 10:
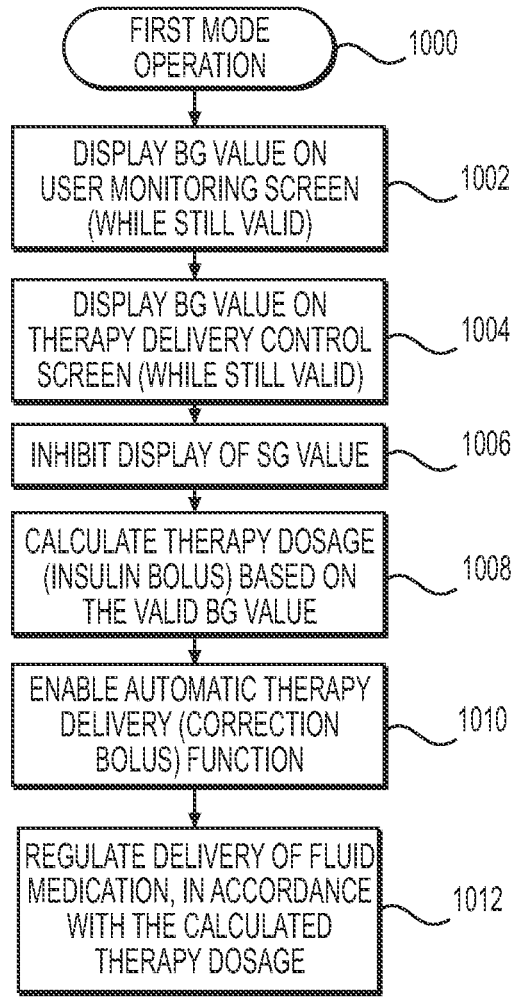
FIG. 10 is a flow chart that illustrates operation of an insulin infusion device in a first mode.

FIG. 10 is a flow chart that illustrates operation of the insulin infusion device in the first mode. The first mode operation process 1000 depicted in FIG. 10 can be performed at task 908 of the process 900.

Figure 11:
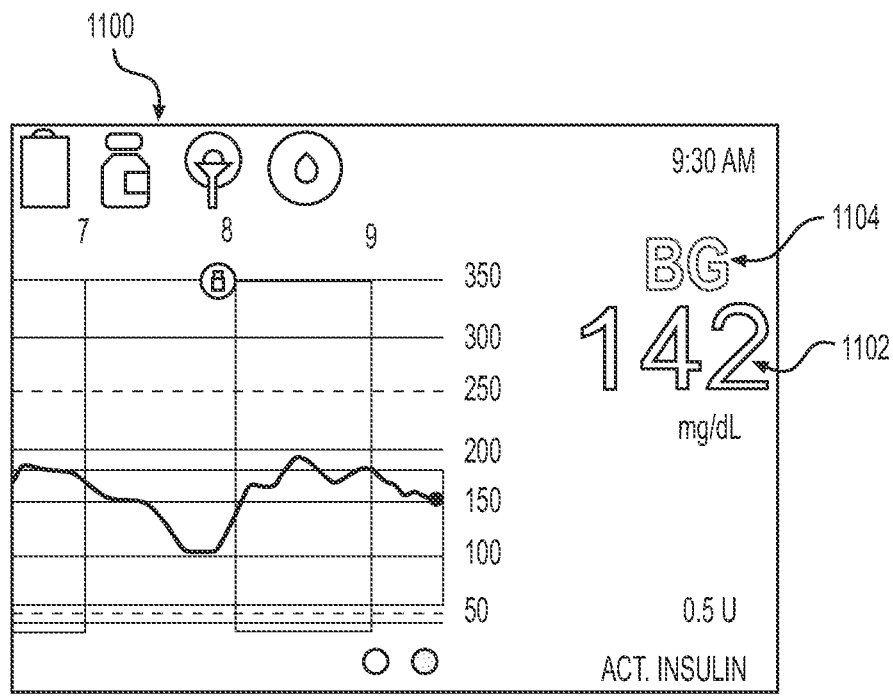
FIG. 11 is a schematic representation of a user monitoring screen on an insulin infusion device, with a meter-generated blood glucose (BG) value displayed thereon.

In this example, a "fresh" BG value is assumed to be accurate and trustworthy. Accordingly, the process 1000 displays the valid BG value on a user monitoring screen of the device (task 1002). This BG value remains displayed on the user monitoring screen while it remains valid. Once the BG value expires or is otherwise deemed to be invalid, it is removed from the user monitoring screen (e.g., ceased to be displayed within the user monitoring screen). In some embodiments, the user monitoring screen is a home screen of the insulin infusion device, and the home screen may include additional information if so desired, such as other patient data, status indicators, etc. In this regard, FIG. 11 is a schematic representation of a user monitoring screen 1100 on an insulin infusion device, with a current and valid meter-generated BG value 1102 displayed thereon. The BG value 1102 can be displayed with a "BG" label 1104 to make it obvious that the displayed value is indeed a BG value (rather than an SG value). Moreover, the process 1000 displays the BG value using visually distinguishable characteristics, which may also be used for displaying the "BG" label 1104 and for displaying the units of the BG value (mg/dL). For example, any one or more of the following visually distinguishable characteristics can be utilized for displaying the BG value: color; font design; font size; font characteristics such as bold, italic, or outlined; animation such as a flashing display or a moving display; fill pattern or stippling; level of transparency; and an accompanying icon (such as a blood drop).

Figure 12:
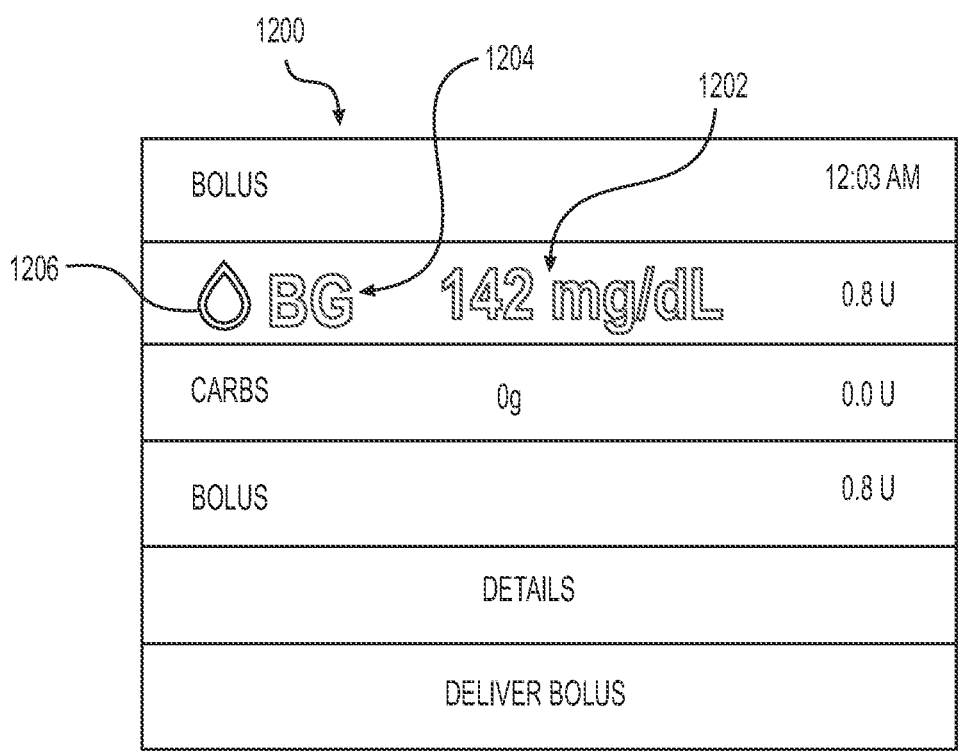
FIG. 12 is a schematic representation of a therapy delivery control screen on an insulin infusion device, with a BG value displayed thereon.

Referring back to FIG. 10, the process 1000 also displays the valid BG value on a therapy delivery control screen of the device (task 1004). The BG value remains displayed on the therapy delivery control screen while it remains valid. Once the BG value expires or is otherwise deemed to be invalid, it is removed from the therapy delivery control screen. For this particular embodiment, the therapy delivery control screen is an insulin bolus delivery control screen of the insulin infusion device, and the bolus delivery control screen may include additional information related to an estimated bolus dosage and the operation of the bolus delivery function. In this regard, FIG. 12 is a schematic representation of a therapy delivery control screen 1200 on an insulin infusion device, with the current and valid BG value 1202 displayed thereon. The BG value 1202 can be displayed with a "BG" label 1204 to make it obvious that the displayed value is indeed a BG value (rather than an SG value). In addition, the BG value 1202 can be displayed with a visually distinguishable and contextually relevant icon 1206 to further indicate that the displayed value is a BG value rather than an SG value. For this example, the icon 1206 resembles a drop of blood, and the icon 1206 is colored red.

Notably, the process 1000 displays the BG value 1202 using the same (or substantially similar) visually distinguishable characteristics used to display the BG value 1102 on the user monitoring screen 1100. The same visually distinguishable characteristics may also be used for displaying the "BG" label 1204 and for displaying the units of the BG value (mg/dL). Using the same visually distinguishable characteristics for the BG value across different user interface screens or features makes it easy for the user to interpret and recognize the source of the displayed glucose measurement. Although this description focuses on the user monitoring screen and the therapy delivery control screen, consistent visual characteristics ("look and feel" aspects) can be used across any number of display screens generated by the device.

Referring back to FIG. 10, the process 1000 inhibits the display of any SG value on the user monitoring screen and on the therapy delivery control screen (task 1006). In this regard, if a valid BG value is available, then the device relies on that measurement, whether or not a current and accurate SG value is also available. Thus, preventing display of an available SG value under these conditions is intuitive and less confusing for users.

The process 1000 continues by calculating therapy dosage (if needed) for delivery, based on the valid meter-generated BG value (task 1008). For this example, an insulin bolus is calculated at task 1008, and the calculated bolus amount is displayed on the therapy delivery control screen. In this regard, the therapy delivery control screen 1200 shown in FIG. 12 includes a calculated insulin bolus of 0.8 Units. Thus, the valid BG value serves as an input or parameter for purposes of estimating an appropriate insulin bolus to maintain the user's blood glucose level within a desired target range.

In some embodiments, the calculated bolus amount can be automatically or manually administered. For example, the bolus can be automatically delivered if automatic delivery mode is supported and active. Accordingly, during operation in the first mode, the process 1000 enables an automatic therapy delivery function of the device (task 1010). Consequently, if the user fails to manually administer the calculated bolus amount, the automatic delivery function will take appropriate action to deliver the bolus in a timely manner. To this end, the process 1000 may automatically control the operation of the device to regulate delivery of the fluid medication (insulin) from the device, in accordance with the calculated therapy dosage (task 1012).

Returning to FIG. 9 and the description of the process 900, if a valid BG value is unavailable (the "No" branch of query task 906), then the process 900 checks the current SG value to determine a measure of quality. The quality of the current SG value can be determined or calculated using any appropriate methodology. For example, the current SG value can be compared against historical SG measurements, historical BG measurements, the most recent BG value, or the like. Additionally or alternatively, the quality of the current SG value can be determined using a "self-diagnostic" technique that considers the age of the continuous glucose sensor, SG measurement trends, electrical noise in the raw sensor signals, etc. In accordance with certain embodiments, the process 900 determines the quality of the SG measurements using the methodology described in more detail below.

Although the quality of SG measurements can be expressed in any suitable manner, the exemplary embodiment of the process 900 considers "high quality" SG measurements to be the best quality (e.g., above a high-quality threshold) and, therefore, appropriate for purposes of glucose monitoring, for therapy dosage calculation, and for controlling the delivery of therapy. The process 900 considers "monitor quality" SG measurements to be appropriate for glucose monitoring only, wherein monitor quality SG measurements are less desirable than high quality SG measurements, yet still suitable for certain non-therapy related functions (e.g., below the high-quality threshold and above a low-quality threshold). If the quality of an SG measurement is deemed to be less than monitor quality (e.g., below the low-quality threshold), then that SG value is neither displayed nor used for therapy related functions.

If the process 900 determines that the current SG value satisfies "high quality" criteria, e.g., quality above the high-quality threshold (the "Yes" branch of query task 910), then the device is controlled in an appropriate manner to operate in a second mode (task 912). In accordance with the embodiment described here, the device is operated in the second mode when a valid meter-generated BG value is unavailable, and when the current sensor-generated SG value is determined to be of high quality.

Figure 13:
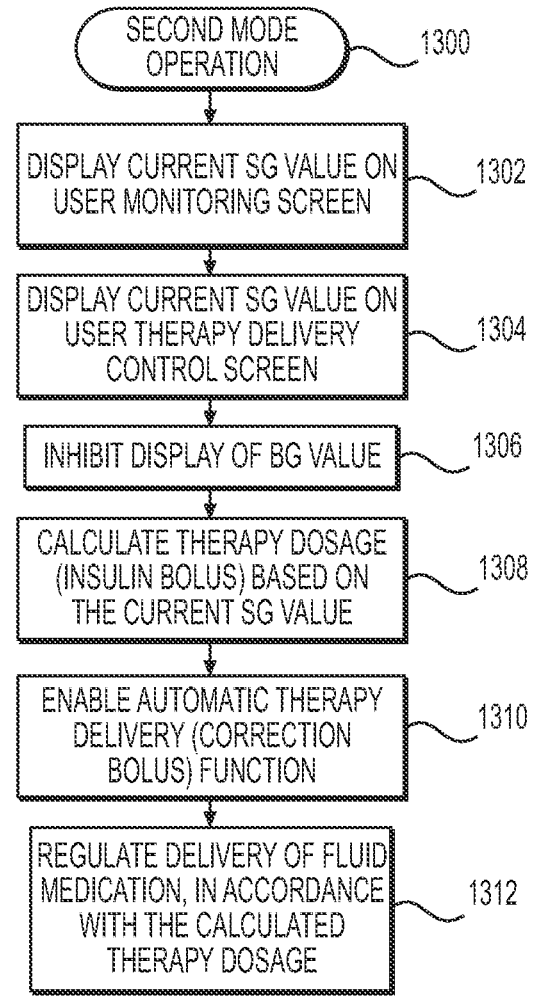
FIG. 13 is a flow chart that illustrates operation of an insulin infusion device in a second mode.
Figure 14:
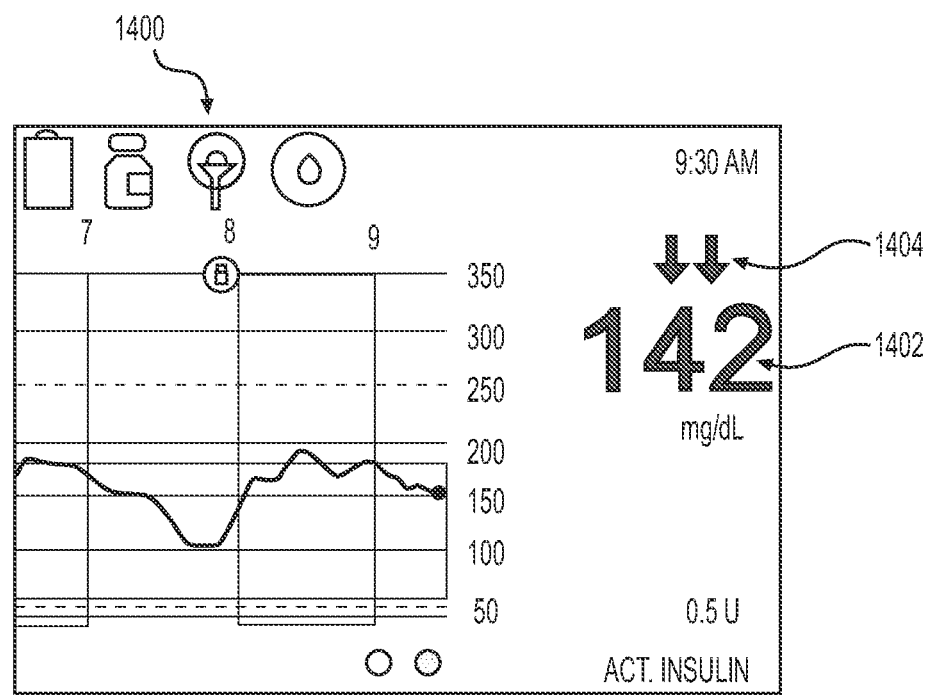
FIG. 14 is a schematic representation of a user monitoring screen on an insulin infusion device, with a sensor-generated glucose (SG) value displayed thereon.

FIG. 13 is a flow chart that illustrates operation of the insulin infusion device in the second mode. The second mode operation process 1300 depicted in FIG. 13 can be performed at task 912 of the process 900. The second mode relies on the high quality SG value, which is currently available for use. Accordingly, the process 1300 displays the current SG value on the user monitoring screen of the device (task 1302). This SG value remains displayed on the user monitoring screen until it is refreshed. FIG. 14 is a schematic representation of a user monitoring screen 1400 on the insulin infusion device, with the current SG value 1402 displayed thereon. The SG value 1402 can be displayed with an "SG" label (not shown) to make it obvious that the displayed value is indeed an SG value (rather than a BG value). The example shown in FIG. 14 displays glucose trend arrows 1404 near the displayed SG value 1402 to indicate whether the user's blood glucose level is increasing or decreasing (e.g., compared to previous glucose level measurements). Moreover, the process 1300 displays the SG value 1402 using visually distinguishable characteristics, which may also be used for displaying the "SG" label, the trend arrows 1404, and the units of the SG value (mg/dL). The embodiment described here uses color as the visually distinguishable characteristic. In some embodiments, however, any one or more of the following characteristics can be utilized for displaying the SG value: color; font design; font size; font characteristics such as bold, italic, or outlined; animation such as a flashing display or a moving display; fill pattern or stippling; level of transparency; and an accompanying icon. Notably, SG values and BG values are displayed using different visually distinguishable characteristics, such that the user can quickly and easily observe whether the displayed measurement is a BG value or an SG value. For example, BG values and related information can be rendered in a white or yellow font, while SG values and related information can be rendered in an obviously contrasting color, such as blue, cyan, or purple.

Figure 15:
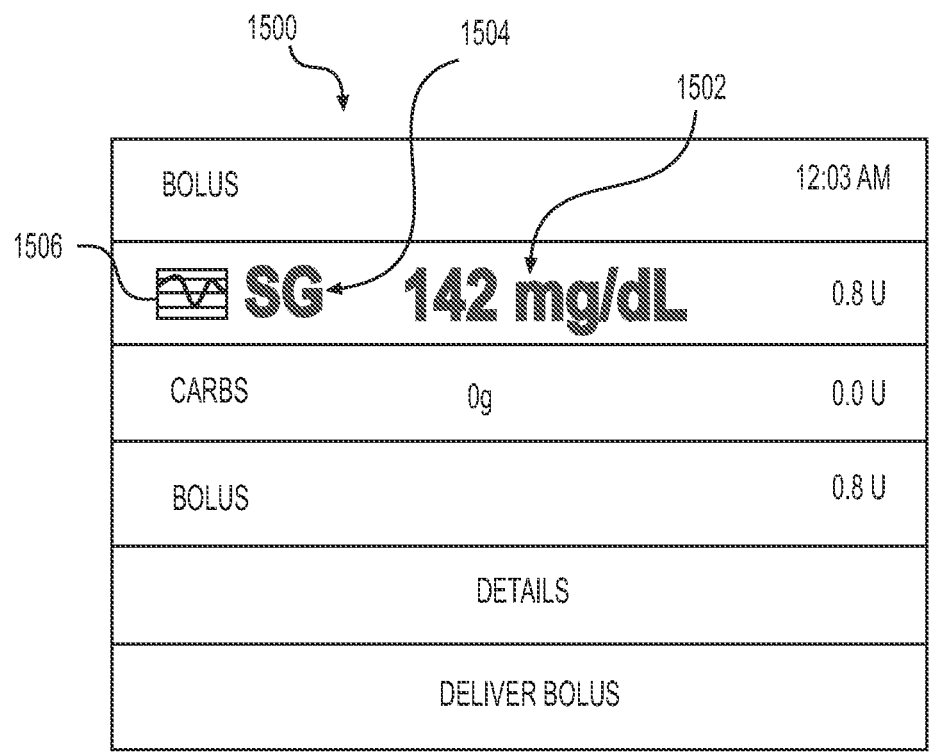
FIG. 15 is a schematic representation of a therapy delivery control screen on an insulin infusion device, with an SG value displayed thereon.

Referring back to FIG. 13, the process 1300 also displays the current SG value on the therapy delivery control screen of the device (task 1304). The SG value remains displayed on the therapy delivery control screen until it gets refreshed, and it cannot be modified via the user interface of the device. FIG. 15 is a schematic representation of a therapy delivery control screen 1500 on an insulin infusion device, with the current (and high quality) SG value 1502 displayed thereon. The SG value 1502 can be displayed with an "SG" label 1504 to make it obvious that the displayed value is indeed an SG value (rather than a BG value). In addition, the SG value 1502 can be displayed with a visually distinguishable and contextually relevant icon 1506 to further indicate that the displayed value is an SG value rather than a BG value. For this example, the icon 1506 resembles a plot or signal waveform, and the icon 1506 is colored to match the color of the displayed SG value 1502.

Notably, the process 1300 displays the SG value 1502 using the same (or substantially similar) visually distinguishable characteristics used to display the SG value 1402 on the user monitoring screen 1400. The same visually distinguishable characteristics may also be used for displaying the "SG" label 1504 and for displaying the units of the SG value (mg/dL). Using the same visually distinguishable characteristics for the SG value across different user interface screens or features makes it easy for the user to interpret and recognize the source of the displayed glucose measurement. Although this description focuses on the user monitoring screen and the therapy delivery control screen, consistent visual characteristics ("look and feel" aspects) can be used across any number of display screens generated by the device.

Referring back to FIG. 13, the process 1300 inhibits the display of any BG value on the user monitoring screen and on the therapy delivery control screen (task 1306). In this regard, if a valid BG value is unavailable, then the device only considers a current (e.g., the most recent) and accurate SG value for display purposes.

The process 1300 continues by calculating therapy dosage (if needed) for delivery, based on the high-quality sensor-generated SG value (task 1308). For this example, an insulin bolus is calculated at task 1308, and the calculated bolus amount is displayed on the therapy delivery control screen. In this regard, the therapy delivery control screen 1500 shown in FIG. 15 includes a calculated insulin bolus of 0.8 Units. Thus, the high quality SG value serves as an input or parameter for purposes of estimating an appropriate insulin bolus to maintain the user's blood glucose level within a desired target range.

In some example, the calculated bolus amount can be manually administered or automatically delivered if automatic delivery mode is supported and active. Accordingly, during operation in the second mode, the process 1300 enables the automatic therapy delivery function of the device (task 1310). Consequently, if the user fails to manually administer the calculated bolus amount, the automatic delivery function will take appropriate action to deliver the bolus in a timely manner. To this end, the process 1300 may automatically control the operation of the device to regulate delivery of the fluid medication (insulin) from the device, in accordance with the calculated therapy dosage (task 1312).

Returning to FIG. 9 and the description of the process 900, if the current SG value does not satisfy the "high quality" criteria (the "No" branch of query task 910), but satisfies "monitor quality" criteria (the "Yes" branch of query task 914), then the device is controlled in an appropriate manner to operate in a third mode (task 916). In accordance with the embodiment described here, the device is operated in the third mode when a valid meter-generated BG value is unavailable, and when the current sensor-generated SG value is determined to be of sufficient quality for user monitoring purposes but potentially unsuitable for calculating therapy dosage.

Figure 16:
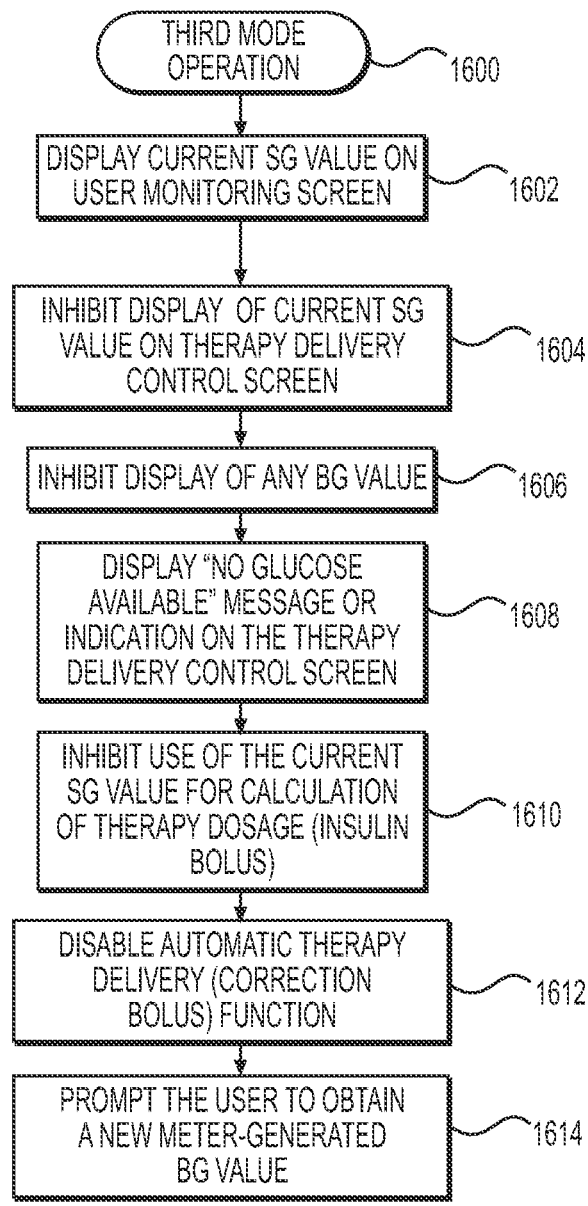
FIG. 16 is a flow chart that illustrates operation of an insulin infusion device in a third mode.

FIG. 16 is a flow chart that illustrates operation of the insulin infusion device in the third mode. The third mode operation process 1600 depicted in FIG. 16 can be performed at task 916 of the process 900. The third mode relies on the monitor quality SG value, which is currently available for use. Accordingly, the process 1600 displays the current SG value on the user monitoring screen of the device (task 1602). This SG value remains displayed on the user monitoring screen until it is refreshed. The above description of the user monitoring screen 1400 (see FIG. 14) also applies to this scenario because the monitor quality SG value is displayed in a similar fashion, with the same visually distinguishable characteristics described previously in connection with the exemplary display shown in FIG. 14.

While operating in the third mode, the device inhibits the display of the current SG value on the therapy delivery control screen (task 1604). In addition, the process 1600 inhibits the display of any BG value on the therapy delivery control screen (task 1606). Instead, the device is operated to display an appropriate message, notification, or indication on the therapy delivery control screen, wherein the displayed content indicates that no suitable measurement of the physiological characteristic of the user is available. For this particular example, the process 1600 displays a message such as "No Glucose" or "No Glucose Available" on the therapy delivery control screen (task 1608). FIG. 17 is a schematic representation of a therapy delivery control screen 1700 on an insulin infusion device, with neither a BG value nor an SG value displayed thereon. Instead, the therapy delivery control screen 1700 includes a "No Glucose" message or field 1702 that lets the user know that no suitable glucose measurement is available for purposes of calculating an estimated bolus. Consequently, the therapy delivery control screen 1700 indicates a bolus amount of 0.0 Units under these conditions.

Referring back to FIG. 16, the process 1600 inhibits the use of the current SG value for purposes of calculating therapy dosage for delivery (task 1610). Although a monitor quality SG value is suitable for use as a general indicator of the user's glucose level, the process 1600 assumes that it is potentially unsuitable for use in calculating a precise insulin bolus amount. Accordingly, the process 1600 operates the device in the third mode to disable the automatic therapy delivery function (task 1612). For the embodiment described here, task 1612 ensures that correction boluses of insulin are not administered while the insulin infusion device is operating in the third mode.

The process 1600 may continue by prompting the user to obtain a new meter-generated BG value (task 1614), which can be used to update the user monitoring screen and the therapy delivery control screen. Moreover, a fresh BG value can be used to calculate an estimated bolus and to reactivate the automatic therapy delivery feature. Additionally or alternatively, the process 1600 may generate a reminder, message, or notification to prompt the user to check the integrity of the sensor device, to recalibrate the sensor device, to replace the sensor device with a new unit, or the like.

Referring again to FIG. 9, if the process 900 determines that the current SG value does not satisfy the designated "monitor quality" criteria (the "No" branch of query task 914), then the process 900 generates an appropriate alert, message, or notification regarding the need to take some form of corrective action (task 918). For example, the device may generate an alert to remind the user to take one or more of the following actions: obtain/enter a new BG value; check the integrity of the currently deployed sensor device; recalibrate the currently deployed sensor device; check the data communication functionality of the currently deployed sensor device; replace the sensor device with a new unit; or the like.

The process 900 is performed in an ongoing manner that contemplates updating of the BG value and/or the SG value over time. The dashed lines in FIG. 9 indicate how the process 900 is repeated as needed to receive and process new BG and SG values.

Automated insulin infusion systems that use feedback from a continuous glucose monitor (CGM) to adjust insulin dosing need to implement safety features to mitigate risk of over-delivery and hypoglycemia under certain glucose sensor conditions. These mitigations may employ one or more of the following technology components: (1) detection and rating of CGM measurement quality for use in automatic insulin dosing; (2) a set of therapy adjustments that are appropriate for each level of sensor quality; (3) a set of system alerts or other user interface (UI) notifications that guide the user to the appropriate action if needed. An example of an insulin infusion system that utilizes a sensor quality metric to adjust therapy delivery modes is described above.

Sensor Quality—A high quality CGM/sensor measurement is needed to realize the full advantages of an automated insulin infusion system to govern basal and bolus insulin deliveries. The sensor quality metric may be determined using known factors that may affect sensor accuracy. Examples of these factors include, without limitation: (1) sensor age that has known correlations to measurement accuracy; (2) measurement noise in the CGM electronics and/or raw sensor signals; (3) a sudden sharp rise or fall in sensor measurement that cannot be attributed to a natural physiological condition.

In accordance with an exemplary embodiment, the sensor quality metric may be mapped onto a scale (e.g., a scale of 1-10, or Low/Medium/High values) that provides different quality grades that can be used to adjust the therapy. The determination of the specific grade should be associated with the potential risk of providing automated therapy given the expected level of sensor error as a result of the underlying condition. For example, transient measurement noise may result in moderate CGM measurement error, so it may correspond to a "medium" sensor quality metric, whereas a sudden, discontinuous jump or drop in a CGM measurement may correspond to a "low" sensor quality metric for purposes of this description.

The sensor quality metric may also depend on characteristics of historical CGM values in a time series. For example, previous CGM values for a moving window of time can be analyzed and compared against the current value. As another example, an average of historical CGM values obtained at or near the same time of day can be analyzed and compared against the current value (obtained at the time of day under analysis). Accordingly, if a sufficient amount of historical values are not available, this condition itself may result in a conservative sensor quality rating until enough historical values are be recorded.

Therapy Adjustments—Once a sensor quality metric is determined, an adjustment to the control algorithm or methodology that governs automated insulin infusion may be necessary to mitigate risks of over or under delivery of insulin. In some embodiments, the specific type of adjustment is dependent on the design of the automated infusion algorithm.

As an example, consider an automated infusion algorithm that uses CGM measurements to make real-time adjustments to basal insulin and provide additional bolus insulin during times of rapidly rising glucose. Furthermore, this algorithm contains a safe fallback delivery mode that provides a constant basal rate for times when the CGM measurement is not available. In such a system, the following cases may be considered for therapy adjustment:

Case 1: "High" CGM/sensor quality metric—The algorithm may use its full authority of basal and bolus insulin based on the CGM measurements.

Case 2: "Medium" CGM/sensor quality metric—Allow only basal insulin delivery to be determined using the CGM but cease or otherwise limit the delivery of bolus insulin.

Case 3: "Low" CGM/sensor quality metric—Ignore the CGM altogether and revert to the safe fallback delivery mode until the sensor quality recovers.

The three cases listed above are representative examples for a hypothetical automated insulin infusion system. A different algorithm design would require therapy adjustments that are matched to the algorithm's dosing rules and/or other factors.

System Alerts and Notifications—System alerts and notifications represent another component to help manage risk while balancing therapy effectiveness and user burden. It is most desirable to maintain acceptable therapy without adding the burden of system alerts that interrupt the user. However, in some cases an alert is necessary to further mitigate risks related to poor CGM quality or to guide the user the action needed to recover optimal therapy.

For example, a particular CGM quality condition may be known to be transient in nature and generally recover without any intervention. In this case it may be appropriate for the system to make the therapy adjustment without notifying the user. However, a condition may be included to notify the user if the CGM quality is not fully recovered after a specified period of time.

As another example, a different CGM quality condition may be known to require a calibration using an external blood glucose measurement to recover. In this case it would be appropriate to alert the user that a CGM calibration is required once this condition occurs.

As mentioned above, the sensor quality metric can be scaled in any desirable manner. In accordance with an exemplary embodiment, the sensor quality metric can be "unknown" or "uncertain" or it can indicate low, medium, or high sensor quality. Table 1 indicates all of the sensor quality metrics for such an implementation, along with their related therapy actions, and system alerts.

TABLE 1

Sensor Quality and Corresponding Actions

| Sensor Quality Metric | Definition | Cause | Therapy Action | User Alert |
|---|---|---|---|---|
| Uncertain | Sensor quality cannot be determined | Insufficient sensor data collected for quality assessment | Deliver automatic basal insulin only; No automatic bolus | None |

TABLE 1-continued

Sensor Quality and Corresponding Actions

| Sensor Quality Metric | Definition | Cause | Therapy Action | User Alert |
|---|---|---|---|---|
| Low | Sensor quality is not reliable for governing therapy | Rapid change due to hardware issues | Revert to safe fallback mode | Request BG measurement for calibration |
| Medium | Sensor quality is appropriate for conservative therapy | New or old sensor; Transient measurement noise; Low sensor sensitivity | Deliver automatic basal insulin; Reduced authority of automatic boluses | None |
| High | Sensor quality is good for full therapy | N/A | Full automated basal and bolus insulin therapy | None |

Figure 18:
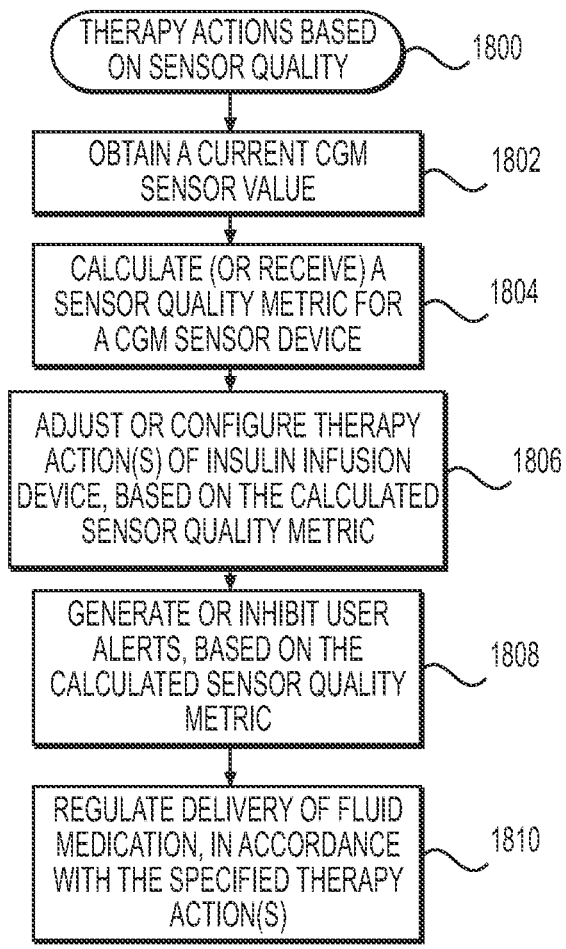
FIG. 18 is a flow chart that illustrates an exemplary embodiment of a method of controlling operation of a medical device to regulate therapy actions based on sensor quality.

FIG. 18 is a flow chart that illustrates an exemplary embodiment of a process 1800 for controlling operation of a medical device to regulate therapy actions based on sensor quality. The process 1800 obtains a current sensor-generated value that is indicative of a physiological characteristic of the user, where the value is produced in response to operation of a continuous analyte sensor device. The embodiment presented here relates to an insulin infusion system that includes or cooperates with a continuous glucose sensor—the physiological characteristic is a glucose level.

The process 1800 obtains a current SG value from a CGM sensor device (task 1802). The process 1800 calculates, receives, or otherwise obtains a sensor quality metric for the CGM sensor device, where the sensor quality metric indicates accuracy, reliability, and/or trustworthiness of the current sensor-generated SG value (task 1804). In accordance with certain embodiments, the sensor quality metric is calculated by the CGM sensor device, which communicates the calculated sensor quality metric to one or more destination devices as needed (for example, the calculated sensor quality metric can be sent from the CGM sensor device to the insulin infusion device, to a glucose monitor device, to a mobile device running a suitably configured mobile app, or the like). Alternatively, or additionally, the sensor quality metric can be calculated by one or more devices other than the CGM sensor device, based on raw sensor signals or information generated at the CGM sensor device. For example, the CGM sensor device can provide its electrical output (such as electrical current values or voltages) to the insulin infusion device, which then calculates the sensor quality metric based on the provided electrical output values.

Figure 20:
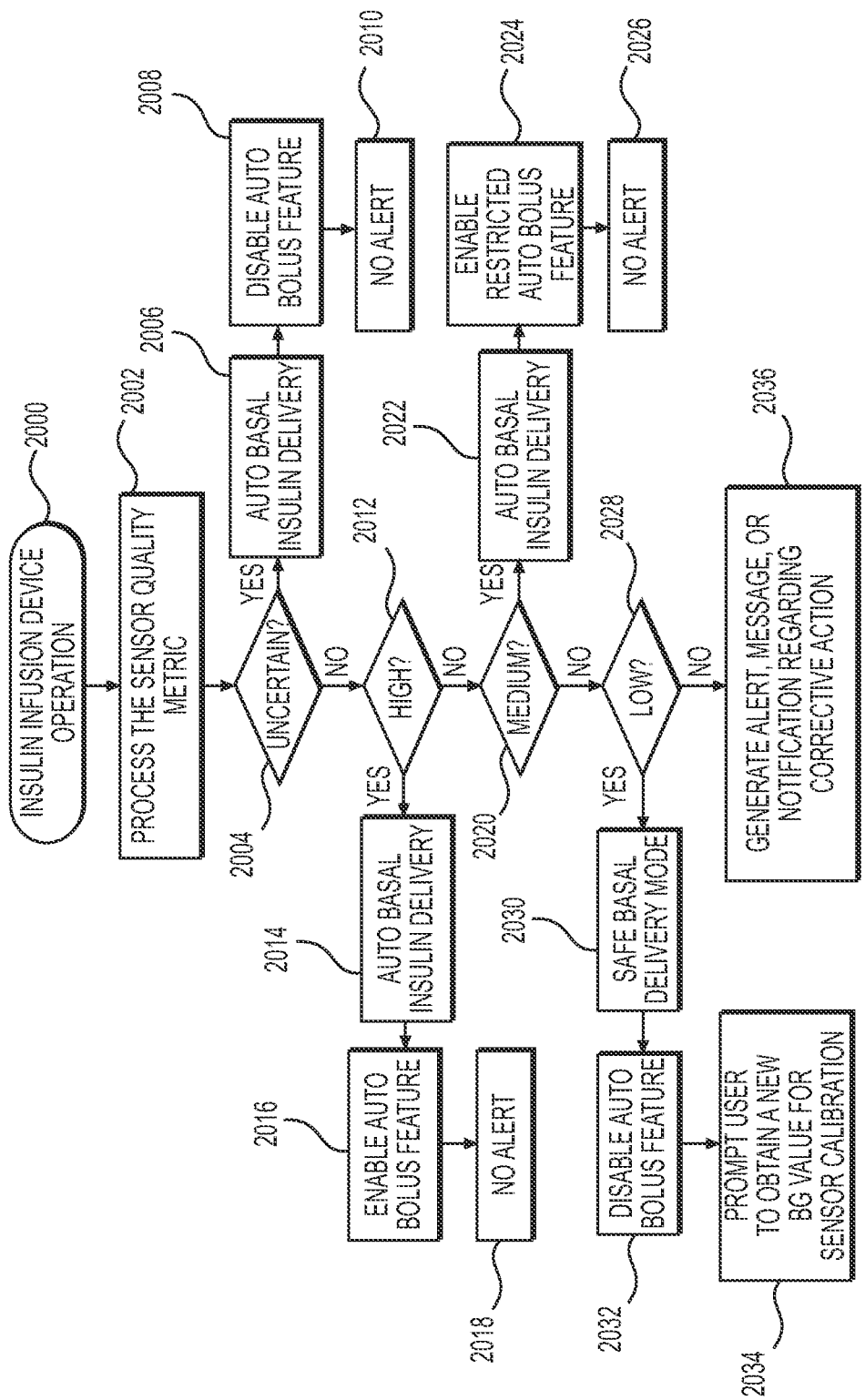
FIG. 20 is a flow chart that illustrates operation of an insulin infusion device in accordance with an exemplary embodiment.

The process 1800 continues by adjusting therapy actions of the insulin infusion device in response to the sensor quality metric, to configure a quality-specific operating mode of the insulin infusion device (task 1806), as described in more detail below with reference to FIG. 20. Thus, therapy-related functions, features, and/or operations of the medical device (the insulin infusion device) are altered based on the calculated sensor quality metric, e.g., high-quality, medium-quality, low-quality, etc. As shown in Table 1, conservative or aggressive insulin therapy options can be enabled/disabled in an ongoing manner, depending on the current state of the sensor quality metric. Moreover, the process 1800 manages the generation of user alerts at the medical device in response to the calculated sensor quality metric (task 1808). In this regard, the process 1800 controls the insulin infusion device (and/or other user devices) to generate, inhibit, or otherwise regulate user alerts, based on the current state of the sensor quality metric. In some embodiments, task 1808 manages alerts by generating user alerts when the calculated sensor quality metric satisfies designated alert-generating criteria, and inhibits user alerts when the calculated sensor quality metric fails the designated alert-generating criteria. The alert-generating criteria can be designated to reduce unwanted or annoyance alerts, alarms, and notifications. For example, the alert-generating criteria may inhibit user alerts if the sensor quality metric is "better" than low. As another example, the alert-generating criteria may permit user alerts if the sensor quality metric is low, or if the system determines that the sensor is at its end of life or has lost communication with the medical device. This provides a better user experience with less nuisance alerts and less worrisome notifications.

The process 1800 continues by regulating delivery of fluid medication (e.g., insulin) from the medical device, in accordance with the current SG value and in accordance with the quality-specific operating mode of the medical device (task 1810). In other words, the delivery of the fluid medication is controlled in response to the current sensor quality metric, which determines the quality-specific operating mode to be used, which results in an adjustment of certain specified therapy actions (see Table 1). For this particular implementation, task 1810 adjusts the therapy actions of the insulin infusion device such that aggressiveness of the insulin delivery therapy is proportional to the quality of the current SG value, as indicated by the calculated sensor quality metric, as described in more detail below with reference to FIG. 20. Depending on the particular application and the type of medical device, the therapy actions can be adjusted, controlled, or regulated in a different manner using any desired methodology or algorithm that is driven by values of the sensor quality metric. The process 1800 can be repeated in an ongoing manner to contemplate updated SG values and their corresponding sensor quality metrics for purposes of adjusting the therapy actions over time.

Figure 19:
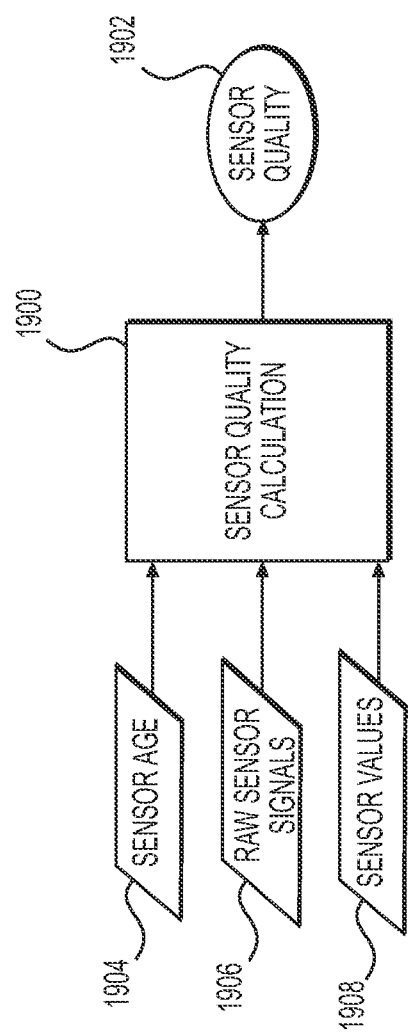
FIG. 19 is a block diagram that illustrates the generation of a sensor quality metric in accordance with an exemplary embodiment.

FIG. 19 is a block diagram that illustrates the generation of a sensor quality metric in accordance with an exemplary embodiment. FIG. 19 depicts sensor quality calculation logic 1900 that calculates the sensor quality metric 1902 from one or more data inputs. The sensor quality calculation logic 1900 may reside and be executed at: the CGM sensor device; the insulin infusion device; a user monitoring device; a mobile device; a smart device or appliance; a cloud-based system, device, or service; a computing system or device onboard a vehicle; a tablet, desktop, or portable computer; or the like. Although not always required, the exemplary embodiment presented here calculates the sensor quality metric 1902 only from information, data, or signals generated by or derived from the continuous analyte sensor device. In other words, the data inputs of the sensor quality calculation logic 1900 are generated by the sensor device or are derived/calculated from data generated by the sensor device, and no information from external calibrating devices or information from ancillary devices is processed by the sensor quality calculation logic 1900 to obtain the sensor quality metric 1902. In this regard, the continuous analyte sensor device can generate its own sensor quality metric 1902 in an "isolated" and self-diagnosing manner without relying on any additional information obtained from another device or system. Alternatively, the continuous analyte sensor device can provide its internally produced or calculated information to a compatible destination device, which then computes the sensor quality metric 1902 using only the information obtained from the sensor device.

In some examples, the data input utilized by the sensor quality calculation logic 1900 may be chosen to suit the needs and requirements of the particular medical device system, the intended application, and/or the specific embodiment. The example shown in FIG. 19 processes at least the following data inputs: sensor age data 1904; raw sensor signal values 1906; and/or historical sensor-generated values 1908 produced in response to operation of the continuous analyte sensor device. As mentioned above, these three data inputs are generated by the sensor device or are derived from information/data generated by the sensor device.

The sensor age data 1904 indicates a chronological age, operating life or "runtime" of the sensor device, the amount of time since deployment of the sensor device, or the like. In this regard, the sensor age data 1904 can be based on the date/time of manufacture, the date/time of initial deployment on the body of the user, the date/time following initialization or warmup of the sensor device following deployment, etc. Preferred implementations base the age of the sensor device on a time immediately following initialization or warmup of the deployed sensor device, which can be determined or marked by the sensor device in certain implementations. The sensor device can keep track of its age and update the sensor age data 1904 in an ongoing manner over time. Alternatively or additionally, the sensor device can mark and report the initial date/time (following warmup), to enable a destination device to keep track of the sensor age and update the sensor age data 1904 as time progresses.

The raw sensor signal values 1906 correspond to the raw signal output of the continuous analyte sensor device, which is produced while the sensor device is monitoring the physiological characteristic of interest. In certain embodiments, the raw sensor signal values 1906 are electrical current and/or electrical voltage measurements. For the continuous glucose sensor example described here, the raw sensor signal values 1906 are electrical current readings that are sometimes referred to as "ISIG" values. The raw sensor signal values 1906 are processed or converted into the monitored analyte levels, such as blood glucose values. To this end, the sensor-generated values 1908 depicted in FIG. 19 represent the usable sensor values that are derived from, calculated from, or converted from the raw sensor signal values 1906. The methodology described here considers a number of historical sensor-generated values 1908 as needed to generate the sensor quality metric 1902 that is associated with the current sensor value.

In certain embodiments, the sensor quality calculation logic 1900 calculates the sensor quality metric 1902 based on: the sensor age data 1904; measurement noise of the raw signal output of the continuous analyte sensor device; and changes in the sensor-generated values 1908 that cannot be attributed to a natural physiological condition of the user. The sensor age data 1904 is considered because accuracy of a newly deployed sensor device usually fluctuates for a short period of time immediately following the initialization or warmup period. Measurement noise in the raw sensor signal values 1906 can be caused by various conditions, such as physical movement of the sensor device, dislodging of the embedded sensor element, sudden unpredictable changes in physiology, ingress of water or other substances at the sensor site, or the like. The raw sensor signal values 1906 are usually relatively stable over "long" periods of time such as five minutes. If, however, the sensor quality calculation logic 1900 detects high variation (measurement noise) in the raw sensor signal values 1906, then the corresponding sensor measurements can be designated as low quality. Similarly, if the sensor-generated values 1908 exhibit sharp changes, spikes, or unrealistic measurements that do not correspond to normal physiological changes or conditions, then the sensor quality calculation logic 1900 can flag those sensor values as low quality or disregard them.

The sensor quality calculation logic 1900 may consider any of the input data items individually or in any combination to generate the sensor quality metric 1902. As mentioned previously, the sensor quality metric 1902 can be expressed in any desired format, using any desired range, scale, or domain. For the exemplary embodiment presented here, the sensor quality metric 1902 is calculated to be a number between 0 and 10 (inclusive), but only four of the available metric values are mapped to the quality states indicated in Table 1: Uncertain; Low; Medium; and High. In other embodiments, more or less than four quality states may be utilized. The sensor quality metric 1902 is generated and formatted in an appropriate manner for compatibility with a fluid medication delivery device, such that therapy actions of the fluid medication delivery device are adjusted in response to the calculated sensor quality metric.

The sensor quality calculation logic 1900 performs a method of assessing operational quality of the continuous analyte sensor device, with the sensor quality metric 1902 serving as an indication of the quality. The sensor quality metric 1902 can be utilized to regulate, control, or adjust certain functions or features of an associated medical device that regulates the delivery of therapy to a patient. In this regard, FIG. 20 is a flow chart that illustrates operation of an insulin infusion device in accordance with an exemplary embodiment (process 2000) for sensor quality calculation logic 1900. The following description of the process 2000 assumes that the insulin infusion device receives or generates sensor quality metrics with corresponding SG values, as described above. Accordingly, the illustrated embodiment of the process 2000 begins by processing the current value of the sensor quality metric (task 2002). For this particular implementation, the process 2000 checks whether the sensor quality metric indicates Uncertain quality (query task 2004), High quality (query task 2012), Medium quality (query task 2020), or Low quality (query task 2028).

When the sensor quality metric indicates Uncertain quality (the "Yes" branch of query task 2004), the process 2000 adjusts certain therapy actions of the insulin infusion device to configure an operating mode that is appropriate for the Uncertain quality status. More specifically, when the sensor quality metric indicates Uncertain quality, the process 2000 enables automatic basal insulin delivery by the insulin infusion device (task 2006), disables an automatic bolus delivery feature of the insulin infusion device (task 2008), and inhibits generation of any user alert related to the current sensor-generated value having Uncertain quality (task 2010). The therapy adjustments made for this particular operating mode are appropriate under the assumption that the sensor quality metric will be determined in the near future. Thus, no user alert is generated, but the automatic bolus delivery function is temporarily disabled.

When the sensor quality metric indicates High quality, e.g., the sensor quality metric is greater than or equal to a high threshold value, such as 7 (the "Yes" branch of query task 2012), the process 2000 adjusts certain therapy actions of the insulin infusion device to configure an appropriate high quality operating mode. More specifically, when the sensor quality metric indicates High quality, the process 2000 enables automatic basal insulin delivery by the insulin infusion device (task 2014), enables the automatic bolus delivery feature (task 2016), and inhibits generation of any user alert related to the current sensor-generated value having high quality (task 2018). The therapy adjustments made for this high quality operating mode are appropriate under the assumption that the sensor device is operating in a normal and accurate manner. To this end, no user alert is generated, and both automatic basal delivery and automatic bolus delivery remain active and enabled.

When the sensor quality metric indicates Medium quality, e.g., the sensor quality metric is between a low threshold value (such as 3) and a high threshold value (such as 7) (the "Yes" branch of query task 2020), the process 2000 adjusts certain therapy actions of the insulin infusion device to configure an appropriate medium quality operating mode. More specifically, when the sensor quality metric indicates Medium quality, the process 2000 enables automatic basal insulin delivery by the insulin infusion device (task 2022), enables a restricted automatic bolus delivery feature (task 2024), and inhibits generation of any user alert related to the current sensor-generated value having medium quality (task 2026). The therapy adjustments made for this medium quality operating mode are appropriate under the assumption that the sensor device is operating in a manner that can still support a modified automatic bolus delivery function. Accordingly, no user alert is generated and automatic basal delivery remains active. However, the automatic bolus delivery function is modified to be less aggressive than usual. For example, the amount of insulin delivered by the automatic bolus delivery function may be limited or capped by some amount, or the bolus amount that is calculated from the current SG value may be reduced by a certain percentage as a safety factor. As another example, when the sensor quality metric indicates Medium quality, the insulin infusion device may be controlled in a way that places an upper limit on the current SG value for purposes of calculating and administering an automatic bolus. In accordance with certain embodiments, when the sensor quality metric indicates Medium quality, a maximum SG value is utilized for purposes of bolus calculation (e.g., 250 mg/dL)—if the current SG value is higher than the maximum allowable SG value, then the actual SG value is disregarded for purposes of automatic bolus calculation. This methodology reduces the likelihood of delivering too much insulin when the reliability or quality of the continuous glucose sensor device is potentially questionable.

When the sensor quality metric indicates Low quality, e.g., the sensor quality metric is less than or equal to a low threshold value, such as 3 (the "Yes" branch of query task 2028), the process 2000 adjusts certain therapy actions of the insulin infusion device to configure an appropriate low quality operating mode. More specifically, when the sensor quality metric indicates Low quality, the process 2000 enables a safe basal insulin delivery mode of the insulin infusion device (task 2030), disables the automatic bolus delivery feature (task 2032), and generates a user alert to prompt the user to take corrective action, such as obtaining a new blood glucose meter value for sensor calibration (task 2034). The therapy adjustments made for this low quality operating mode result in conservative insulin therapy. To this end, the normal basal insulin delivery profile for the user may be adjusted to be generally less aggressive, or the basal delivery profile may be adjusted to be a flat profile that merely provides a baseline amount of basal insulin over time. Moreover, automatic bolus delivery is suspended until the sensor quality metric improves.

As outlined above, low aggressiveness in the fluid medication therapy is provided when the sensor quality metric is low (e.g., at or below a low threshold value), medium aggressiveness is provided when the sensor quality metric is medium (e.g., between the low threshold value and a high threshold value), and high aggressiveness is provided when the sensor quality metric is high (e.g., at or above the high threshold value). Depending on the implementation, more or less than three levels of aggressiveness may be supported.

If the sensor quality metric indicates quality worse than Low quality, or indicates an erroneous value, then the process 2000 may generate an appropriate alert, message, or notification regarding the need to investigate, take corrective action, or the like (task 2036). For example, the insulin infusion device may generate an audible alert and display a message that asks the user to check the integrity of the sensor device, recalibrate the sensor device, replace the sensor device, etc.

An iteration of the process 2000 can be performed as often as needed in an ongoing manner. In some embodiments, the process 2000 is performed for each new SG value (and its corresponding sensor quality metric).

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or other form of executable program instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

The various tasks performed in connection with a process described herein may be performed by software, hardware, firmware, or any combination thereof. It should be appreciated that a described process may include any number of additional or alternative tasks, the tasks shown in a flow chart representation need not be performed in the illustrated order, and that a described process may be incorporated into a more comprehensive procedure or process having additional functionality not described in detail herein. Moreover, one or more of the illustrated tasks could be omitted from an embodiment of the described process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A processor-implemented method comprising:
    obtaining a current sensor-generated value that is indicative of a physiological characteristic of a user of a medical device, the current sensor-generated value produced in response to operation of a continuous analyte sensor device;
    obtaining a sensor quality metric that indicates accuracy of the current sensor-generated value;
    causing, in response to obtaining the sensor quality metric, configuration of a quality-specific operating mode of the medical device, the quality-specific operating mode comprising separate regulation of basal and bolus deliveries of a fluid medication based on the obtained sensor quality metric; and
    causing regulation of fluid medication delivery from the medical device, in accordance with the current sensor-generated value and the quality-specific operating mode of the medical device.

2. The method of claim 1, wherein the sensor quality metric is calculated from information generated by or derived from the continuous analyte sensor device.

3. The method of claim 2, wherein the information comprises sensor age data, raw sensor signal values, and historical sensor-generated values produced in response to operation of the continuous analyte sensor device.

4. The method of claim 1, further comprising managing generation of user alerts at the medical device in response to the obtained sensor quality metric.

5. The method of claim 4, wherein managing generation of user alerts comprises:
    generating user alerts when the obtained sensor quality metric satisfies alert-generating criteria; and
    inhibiting the user alerts when the calculated sensor quality metric fails the alert-generating criteria.

6. The method of claim 1, wherein:
    the sensor quality metric is calculated by the continuous analyte sensor device;
    the current sensor-generated value is obtained by the medical device; and
    the method further comprises communicating the calculated sensor quality metric from the continuous analyte sensor device to the medical device.

7. The method of claim 1, wherein obtaining the sensor quality metric comprises calculating the sensor quality metric based on:
    sensor age data that indicate age of the continuous analyte sensor device;
    measurement noise of raw signal output of the continuous analyte sensor device; and
    changes in sensor-generated values that cannot be attributed to a natural physiological condition of the user.

8. The method of claim 1, wherein when the sensor quality metric indicates an uncertain quality, the quality-specific operating mode enables automatic basal delivery by the medical device, disables an automatic bolus delivery feature of the medical device, and inhibits generation of any user alert related to the current sensor-generated value having uncertain quality.

9. The method of claim 1, wherein when the sensor quality metric indicates high quality, the quality-specific operating mode enables automatic basal delivery by the medical device, enables an automatic bolus delivery feature of the medical device, and inhibits generation of any user alert related to the current sensor-generated value having high quality.

10. The method of claim 1, wherein when the sensor quality metric indicates medium quality, the quality-specific operating mode enables automatic basal delivery by the medical device, enables a restricted automatic bolus delivery feature of the medical device, and inhibits generation of any user alert related to the current sensor-generated value having medium quality.

11. The method of claim 1, wherein when the sensor quality metric indicates low quality, the quality-specific operating mode enables a safe basal delivery mode of the medical device, disables an automatic bolus delivery feature of the medical device, and generates a user alert to prompt the user to take corrective action.

12. The method of claim 11, wherein the user alert prompts the user to calibrate the continuous analyte sensor device.

13. The method of claim 1, wherein causing configuration of the quality-specific operating mode comprises causing adjustment of therapy actions of the medical device such that aggressiveness of fluid medication therapy is proportional to quality of the current sensor-generated value as indicated by the calculated sensor quality metric.

14. The method of claim 1, wherein:
    the medical device is an insulin infusion device;
    the fluid medication comprises insulin;
    the physiological characteristic of the user is a glucose level; and
    the continuous analyte sensor device is a continuous glucose sensor device.

15. One or more non-transitory processor-readable media storing instructions which, when executed by one or more processors, cause performance of:
    obtaining a current sensor-generated value that is indicative of a physiological characteristic of a user of a medical device, the current sensor-generated value produced in response to operation of a continuous analyte sensor device;
    obtaining a sensor quality metric that indicates accuracy of the current sensor-generated value;
    causing, in response to obtaining the sensor quality metric, configuration of a quality-specific operating mode of the medical device, the quality-specific operating mode comprising separate regulation of basal and bolus deliveries of a fluid medication based on the obtained sensor quality metric; and causing regulation of fluid medication delivery from the medical device, in accordance with the current sensor-generated value and the quality-specific operating mode of the medical device.

16. A system comprising:

one or more processors; and one or more processor-readable media storing instructions which, when executed by one or more processors, cause performance of:

obtaining a current sensor-generated value that is indicative of a physiological characteristic of a user of a medical device, the current sensor-generated value produced in response to operation of a continuous analyte sensor device;

obtaining a sensor quality metric that indicates accuracy of the current sensor-generated value;

causing, in response to obtaining the sensor quality metric, configuration of a quality-specific operating mode of the medical device, the quality-specific operating mode comprising separate regulation of basal and bolus deliveries of a fluid medication based on the obtained sensor quality metric; and causing regulation of fluid medication delivery from the medical device, in accordance with the current sensor-generated value and the quality-specific operating mode of the medical device.

17. The system of claim 16, wherein the sensor quality metric is obtained from the continuous analyte sensor device.

18. The system of claim 16, wherein the medical device calculates the sensor quality metric from information generated by or derived from the continuous analyte sensor device, the information comprising:

sensor age data that indicate age of the continuous analyte sensor device;

measurement noise of raw signal output of the continuous analyte sensor device; and changes in sensor-generated values that cannot be attributed to a natural physiological condition of the user.

19. The system of claim 16, wherein:

when the sensor quality metric indicates an uncertain quality, the quality-specific operating mode enables automatic basal delivery by the medical device, disables an automatic bolus delivery feature of the medical device, and inhibits generation of any user alert related to the current sensor-generated value having uncertain quality;

when the sensor quality metric indicates high quality, the quality-specific operating mode enables automatic basal delivery by the medical device, enables the automatic bolus delivery feature, and inhibits generation of any user alert related to the current sensor-generated value having high quality;

when the sensor quality metric indicates medium quality, the quality-specific operating mode enables automatic basal delivery by the medical device, enables a restricted automatic bolus delivery feature, and inhibits generation of any user alert related to the current sensor-generated value having medium quality; and when the sensor quality metric indicates low quality, the quality-specific operating mode enables a safe basal delivery mode of the medical device, disables the automatic bolus delivery feature, and generates a user alert to prompt the user to take corrective action.

20. The system of claim 16, wherein causing configuration of the quality-specific operating mode comprises causing adjustment of therapy actions of the medical device such that aggressiveness of fluid medication therapy is proportional to quality of the current sensor-generated value as indicated by the sensor quality metric.

* * * * *